United States Patent
Elias et al.

(10) Patent No.: US 11,717,528 B2
(45) Date of Patent: *Aug. 8, 2023

(54) METHODS AND COMPOSITIONS RELATING TO THE TREATMENT OF FIBROSIS

(71) Applicant: BROWN UNIVERSITY, Providence, RI (US)

(72) Inventors: Jack A. Elias, Providence, RI (US); Chun Geun Lee, Woodbridge, CT (US); Chang-Min Lee, Warwick, RI (US)

(73) Assignee: BROWN UNIVERSITY, Providence, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/571,295

(22) Filed: Jan. 7, 2022

(65) Prior Publication Data
US 2022/0117987 A1 Apr. 21, 2022

Related U.S. Application Data

(63) Continuation of application No. 16/639,462, filed as application No. PCT/US2018/046845 on Aug. 17, 2018, now Pat. No. 11,219,630.

(60) Provisional application No. 62/546,687, filed on Aug. 17, 2017.

(51) Int. Cl.
*A61K 31/7034* (2006.01)

(52) U.S. Cl.
CPC ................................ *A61K 31/7034* (2013.01)

(58) Field of Classification Search
None
See application file for complete search history.

(56) References Cited

U.S. PATENT DOCUMENTS

| | | | |
|---|---|---|---|
| 3,358,001 A | 12/1967 | Hamao et al. | |
| 3,480,614 A | 11/1969 | Cron et al. | |
| 3,856,969 A | 12/1974 | Takeuchi et al. | |
| 2003/0113330 A1* | 6/2003 | Uhal ................ | A61K 31/56 514/177 |

FOREIGN PATENT DOCUMENTS

| | | |
|---|---|---|
| CN | 107223663 B | 10/2019 |
| EP | 2835426 B1 | 9/2016 |
| WO | 03/009808 A2 | 2/2003 |
| WO | 2017/066712 A2 | 4/2017 |
| WO | 2019/036566 A1 | 2/2019 |

OTHER PUBLICATIONS

Extended European Search Report received for European Patent Application No. 18847112.2, dated Apr. 6, 2021, 11 pages.
International Search Report and Written Opinion received for PCT Application No. PCT/US2018/046845, dated Nov. 20, 2018, dated Nov. 20, 2018, 10 pages.
Bhagirath et al., "Cystic Fibrosis Lung Environment and Pseudomonas Aeruginosa Infection", BMC Pulmonary Medicine, vol. 16, No. 174, 2016, pp. 1-22.
Hiro et al., "The Effect of Kasugamycin (KSM) on Respiratory-Tract Infection with Pseudomonas Aeruginosa", Iryo, vol. 21, No. 8, 1967, pp. 906-911.
Hong et al., "Chitotriosidase Inhibits Allergic Asthmatic Airways via Regulation of TGF-Beta Expression and Foxp3(+) Treg Cells", Allergy, vol. 73, No. 8, 2018, pp. 1686-1699.
Kitamoto, et al., "Kasugamycin—Basic and Clinical Studies", Chemotherapy, vol. 15, No. 1, Jan. 25, 1967, pp. 30-36.
Lee, et al., "Chitinase 1 Is a Biomarker for and Therapeutic Target in Scleroderma-Associated Interstitial Lung Disease That Augments TGF-β1 Signaling", Journal of Immunology, vol. 189, No. 5, doi:10.4049/jimmunol.1201115, Sep. 1, 2012, pp. 2635-2644.
Lee, et al., "Kasugamycin is a Novel Chitinase 1 Inhibitor with Strong Antifibrotic effects on Pulmonary Fibrosis", Feb. 26, 2021, pp. 1-32.
Oku, et al., "Antifibrotic Action of Pirfenidone and Prednisolone: Different Effects on Pulmonary Cytokines and Growth Factors in Bleomycin-induced Murine Pulmonary Fibrosis", European Journal of Pharmacology, vol. 590, 2008, pp. 400-408.

* cited by examiner

*Primary Examiner* — Layla D Berry
(74) *Attorney, Agent, or Firm* — Adler Pollock & Sheehan P.C.; Michel Morency

(57) ABSTRACT

Described herein are methods of treating fibrosis and fibrotic diseases with certain aminoglycosides, e.g., kasugamycin derivatives thereof.

5 Claims, 13 Drawing Sheets

Specification includes a Sequence Listing.

METHODS AND COMPOSITIONS RELATING TO THE TREATMENT OF FIBROSIS

CROSS-REFERENCE TO RELATED APPLICATIONS

This application is a continuation of U.S. patent application Ser. No. 16/639,462 filed Feb. 14, 2020, which is a national phase filing under 35 U.S.C. § 371 of International Application No. PCT/US2018/046845 filed Aug. 17, 2018, which claims benefit under 35 U.S.C. § 119(e) of U.S. Provisional Application No. 62/546,687 filed Aug. 17, 2017, the contents of which are incorporated herein by reference in their entirety.

GOVERNMENT SUPPORT

This invention was made with government support under Grant No. RO1 HL 115813 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Sep. 28, 2018, is named 058040-089240WOPT_SL.txt and is 14 kilobytes in size.

TECHNICAL FIELD

The technology described herein relates to the treatment of fibrotic diseases.

BACKGROUND

Fibrosis is an underlying cause of mortality and morbidity in a number of diseases, including fibrotic diseases of the lung. Therapeutic approaches that directly address the mechanisms of fibrosis (e.g., increases in collagen) are necessary in order to counter the causes of such diseases and provide effective treatment.

SUMMARY

As described herein, the inventors have discovered that kasugamycin, a previously known antibiotic, displays unexpected activity in inhibiting the mechanisms of fibrosis. This activity is unqiue to kasugamycin and is not displayed by other aminoglycoside antibiotics.

In one aspect of any of the embodiments, described herein is a method of treating a fibrotic disease in a subject in need thereof, the method comprising administering kasugamycin or derivatives thereof to the subject. In some embodiments of any of the aspects, the method comprises administering kasugamycin.

In some embodiments of any of the aspects, the morbidity and mortality of the disease is characterized by tissue fibrosis. In some embodiments of any of the aspects, the fibrotic disease is characterized by etiological fibrosis. In some embodiments of any of the aspects, the fibrotic disease is not cystic fibrosis. In some embodiments of any of the aspects, the fibrotic disease is pulmonary fibrosis. In some embodiments of any of the aspects, the fibrotic disease is associated with abnormalities in Chitinase 1 (Chit1) and or a Chit1-mediated fibrotic disease. In some embodiments of any of the aspects, the fibrotic disease is selected from the group consisting of: idiopathic pulmonary fibrosis; scleroderma; scleroderma of the skin; scleroderma of the lungs; a collagen vascular disease; lupus; rheumatoid arthritis; scleroderma; genetic pulmonary fibrosis; Hermansky-Pudlak Syndrome; radiation pneumonitis; asthma; asthma with airway remodeling; chemotherapy-induced pulmonary fibrosis; radiation fibrosis; Gaucher's disease; fibrosis in a subject with Gaucher's disease or the fibrotic component of Gaucher's disease; interstitial lung disease; retroperitoneal fibrosis; myelofibrosis; interstitial or pulmonary vascular disease; fibrosis or interstitial lung disease associated with drug exposure; interstitial lung disease associated with exposures such as asbestosis, silicosis, and grain exposure; chronic hypersensitivity pneumonitis; an adhesion; an intestinal or abdominal adhesion; cardiac fibrosis; kidney fibrosis; cirrhosis; nonalcoholic steastohepatitis (NASH); and nonalcoholic steastohepatitis (NASH) with liver fibrosis. In some embodiments of any of the aspects, the treatments described herein treat fibrosis in a subject having or diagnosed as having one of the conditions described herein. In some embodiments of any of the aspects, the treatments described herein reduce fibrosis or symptoms of fibrosis in a subject having or diagnosed as having one of the conditions described herein. In some embodiments of any of the aspects, the the compositions described herein are administered at a dose sufficient to treat or reduce fibrosis in a subject having or diagnosed as having one of the conditions described herein.

In some embodiments of any of the aspects, the subject has been determined to have an increased level of Chit1 and/or Chit1 activity.

BRIEF DESCRIPTION OF THE DRAWINGS

FIG. 3A depicts the results of a lung collagen assay by Sircol. FIG. 3B depicts results of RT-PCR assay of selected extracellular matrix genes on lung lysate $*p<0.05$, $**p<0.01$ by ANOVA evaluation, Bleo, bleomycin; KSM, kasugamycin.

FIG. 12A depicts a schematic illustration of the experiemental procedure. Bleomycin was given IP for 5 consecutive days followed by kasugamycin at 50 mg/kg qod for 7 days starting on day 12. FIG. 12B depicts a graph of the effects on fibrosis (collagen accumulation).

FIG. 13A depicts a schematic illustration of the experimental procedure. Pulmonary fibrosis was induced in WT C57BL/6 mice by injecting bleomycin 6 times intra-peritoneal (IP) injection (25 unit/kg) daily (day 1-6). Units/injection—100 uL of 6 U/mL bleomycin solution (0.6 unit/injection). Kasugamycin was then administered at 50 mg/kg, 100 mg/kg, or 500 mg/kg, gavage everyday. FIG. 13B depicts a graph of the effects on collagen count. The x-axis specifies the dose of kasugamcyin used.

DETAILED DESCRIPTION

Figure 1:
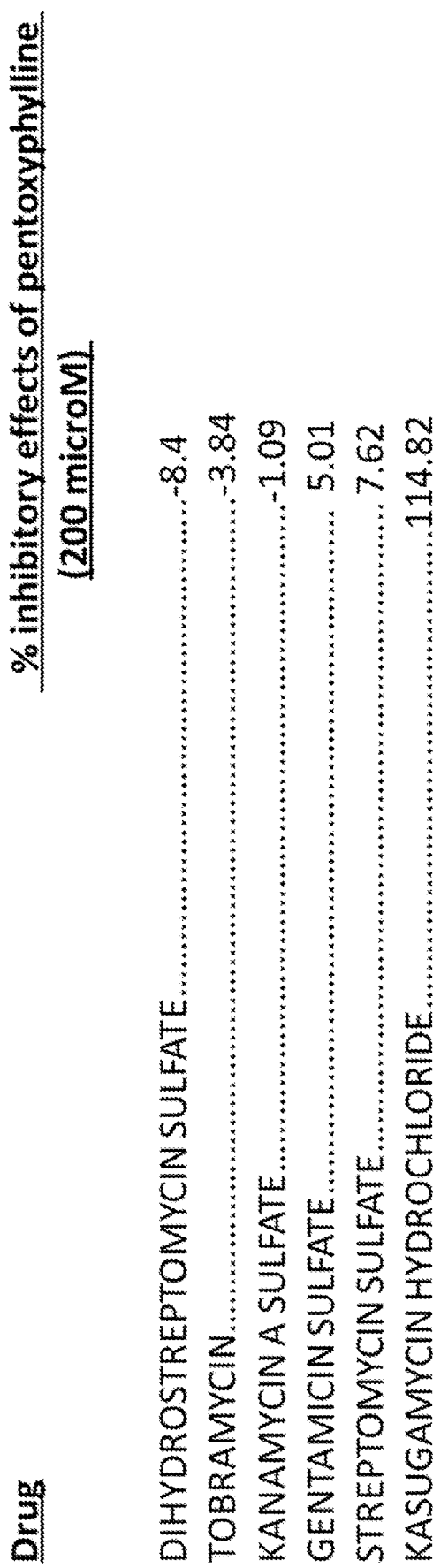
FIG. 1 demonstrates the % inhibition of Chit1 of a number of aminoglycosides and that among aminoglycoside antibiotics. Kasugamycin is unique in its ability to inhibit chitotriosidase activity.

In one aspect of any of the embodiments, described herein is a method of treating a fibrotic disease in a subject in need thereof, the method comprising administering kasugamycin or derivatives, analogs, or variants thereof to the subject. In one aspect of any of the embodiments, described herein is a method of treating a fibrotic disease in a subject in need thereof, the method comprising administering kasugamycin to the subject.

As used herein, "fibrosis" refers to the formation of fibrous tissue as a reparative or reactive process, rather than as a normal constituent of an organ or tissue. Fibrosis is characterized by fibroblast accumulation and collagen deposition in excess of normal deposition in any particular tissue. Fibrosis can occur as the result of inflammation, irritation, or healing. As used herein "fibrotic disease" refers to a disease characterized by and arising from pathological fibrosis. In some embodiments of any of the aspects, the morbidity and mortality of the disease is characterized by tissue fibrosis. In some embodiments of any of the aspects, the fibrotic disease is characterized by etiological fibrosis. In some embodiments of any of the aspects, the methods described herein reduce collagen levels at the site of the fibrotic disease, and/or reduce the rate of collagen deposition at the site of the fibrotic disease.

In some embodiments of any of the aspects, the fibrotic disease is pulmonary fibrosis. Non-limiting examples of fibrotic diseases can include idiopathic pulmonary fibrosis; scleroderma; scleroderma of the skin; scleroderma of the lungs; a collagen vascular disease (e.g., lupus; rheumatoid arthritis; scleroderma); genetic pulmonary fibrosis (e.g., Hermansky-Pudlak Syndrome); radiation pneumonitis; asthma; asthma with airway remodeling; chemotherapy-induced pulmonary fibrosis (e.g., bleomycin, methotrextate, or cyclophosphamide-induced); radiation fibrosis; Gaucher's disease; interstitial lung disease; retroperitoneal fibrosis; myelofibrosis; interstitial or pulmonary vascular disease; fibrosis or interstitial lung disease associated with drug exposure; interstitial lung disease associated with exposures such as asbestosis, silicosis, and grain exposure; chronic hypersensitivity pneumonitis; an adhedsion; an intestinal or abdominal adhesion; cardiac fibrosis; kidney fibrosis; cirrhosis; and nonalcoholic steastohepatitis (NASH)-induced fibrosis.

In some embodiments of any of the aspects, the fibrotic disease is not cystic fibrosis.

The pathoglogy of certain fibrotic diseases is associated with and/or caused by misregulation of and/or mutation of Chit1. In some embodiments of any of the aspects, the fibrotic disease treated according to the methods described herein is a fibrotic disease is associated with abnormalities in Chitinase 1 (Chit1) and or a Chit1-mediated fibrotic disease, e.g., scleroderma; interstitial lung disease, chemotherapy-induced pulmonary fibrosis, kidney fibrosis, and acute kidney injury.

The pathology of many fibrotic diseases is associated with abnormalities in Transforming Growth Factor Beta 1 (TGFβ1) (e.g., NCBI Gene ID 7040), e.g, overexpression of TGFβ1 and/or abnormally high activity of TGFβ1. The role of TGFβ1 in such disease is known in the art, for example, see Meng et al. Nat Rev Nephol 12:325-338 (2016); Branton and Kopp. Microbes Infect 1:1349-1365 (1999); Biernacka et al. Growth Factors 29:196-202 (2011); Pohlers et al. Biochemica et Biophysica Acta 1792:746-756 (2009); each of which is incorporated by reference herein. As demonstrated herein, kasugamycin can inhibit Chit1, and Chit1 inhibits SMAD7, while SMAD7 inhibits TGFβ1. Accordingly, the methods described herein can be used to treat any disease associated with abnormal TGFβ1 levels and/or activity, e.g., misregulated and/or mutated TGFβ1. Non-limiting examples of fibrotic disease associated with TGFβ1, e.g., associated with abnormalities in TGFβ1 can include kidney disease, kidney fibrosis, hepatic fibrosis, cardiac fibrosis, pulmonary fibrosis, dermal fibrosis, renal interstitial fibrosis, arthritis, diabetic nephropathy, colitis, Crohn's disease, radiation-induced fibrosis, myocarditis, and rheumatoid arthritis.

Kasugamycin (e.g., a compound of formula I) can also be referred to in the art as 2-amino-2-[(2R,3S,5S,6R)-5-amino-2-methyl-6-[(2R,3S,5S,6S)-2,3,4,5,6-pentahydroxycyclohexyl]oxyoxan-3-yl]iminoacetic acid; Kasumin; or 3-O-[2-Amino-4-[carboxyiminomethyl)amino]-2,3,4,6-tetradeoxy-D-arabino-hexopyranosyl]-D-chiro-inositol.

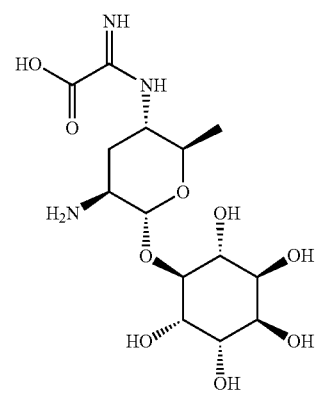 [SMILES: C[C@H]1O[C@H](O[C@H]2[C@H](O)[C@@H](O)[C@@H](O)[C@H](O)[C@@H]2O)[C@@H](N)C[C@@H]1NC(=N)C(=O)O]

Formula I As used herein, a molecule is said to be a "derivative" of another molecule when it contains additional chemical moieties not normally a part of the molecule and/or when it has been chemically modified. Such moieties can improve the molecule's expression levels, enzymatic activity, solubility, absorption, biological half-life, etc. The moieties can alternatively decrease the toxicity of the molecule, eliminate or attenuate any undesirable side effect of the molecule, etc. Moieties capable of mediating such effects are disclosed in Remington's Pharmaceutical Sciences, 18th edition, A. R. Gennaro, Ed., MackPubl., Easton, Pa. (1990). A "variant" of a molecule is meant to refer to a molecule substantially similar in structure and function to either the entire molecule, or to a fragment thereof. A molecule is said to be "substantially similar" to another molecule if both molecules have substantially similar structures and/or if both molecules possess a similar biological activity. Thus, provided that two molecules possess a similar activity, they are considered variants as that term is used herein even if the structure of one of the molecules not found in the other, or if the structure is not identical. An "analog" of a molecule is meant to refer to a molecule substantially similar in function to either the entire molecule or to a fragment thereof.

Non-limiting examples of kasugamycin derivatives include those described in U.S. Pat. Nos. 3,968,100; 4,554,269; 5,317,095; and 3,480,614; each of which is incorporated by reference herein in its entirety.

In some embodiments of any of the aspects, the subject treated according to the methods described herein is a subject determined to have an increased level of Chitinase 1 (Chit1), e.g., an increased level of Chit1 expression product and/or Chit1 activity. In some embodiments of any of the aspects, the method described herein can further comprise a first step of determining the level of Chit1 in a subject in need of treatment for a fibrotic disease, and administering kasugamycin or a derivative, analog, or variant thereof if an increased level of Chit1 is detected.

As used herein, "chitinase 1," "Chitotriosidase," or "Chit1" refers to a chitinase that degrades chitin, chitotriose, and chitobioise via endo-hydrolysis of N-acetyl-beta-D-glucosaminide (1->4)-beta-linkages in chitin and chitodextrins. The sequences of Chit1 expression products are known for a number of species, e.g., human Chit1 (NCBI Gene ID No: 1118) mRNA (SEQ ID NO: 1; NCBI Ref Seq: NM_001256125.1 and SEQ ID NO: 2; NCBI Ref Seq: NM_003465.2) and polypeptide (SEQ ID NO: 3; NCBI Ref Seq: NP_001243054.2 and SEQ ID NO: 4; NCBI Ref Seq: NP_003456.1). Chit1 can also refer to natural variants, alleles, homologs, and/or orthologs of the particular sequences provided herein, each of which are readily identified by one of skill in the art. The activity of Chit1 can be measured, e.g., by measuring its ability to hydrolyze a fluorogenic substrate, e.g., as described in Lee et al. 2012 Journal of Immunology 189:2635-2644; which is incorporated by reference herein in its entirety.

The level of Chit1 can be determined, e.g., by measuring/detecting the presence or intensity of a signal which indicates the presence or level of Chit1 in the sample. In some embodiments of any of the aspects, the level of Chit1 can be determined, e.g., by, (a) transforming the Chit1 into a detectable target; (b) measuring the amount of the target; and (c) comparing the amount of the gene target to an amount of a reference.

As used herein, the term "transforming" or "transformation" refers to changing an object or a substance, e.g., biological sample, nucleic acid or protein, into another substance. The transformation can be physical, biological or chemical. Exemplary physical transformation includes, but not limited to, pre-treatment of a biological sample, e.g., from whole blood to blood serum by differential centrifugation. A biological/chemical transformation can involve at least one enzyme and/or a chemical reagent in a reaction. For example, a DNA sample can be digested into fragments by one or more restriction enzyme, or an exogenous molecule can be attached to a fragmented DNA sample with a ligase. In some embodiments of any of the aspects, a DNA sample can undergo enzymatic replication, e.g., by polymerase chain reaction (PCR).

Transformation, measurement, and/or detection of a target molecule, e.g. a Chit1 mRNA or polypeptide can comprise contacting a sample obtained from a subject with a reagent (e.g. a detection reagent) which is specific for the target, e.g., a Chit1-specific reagent. In some embodiments of any of the aspects, the target-specific reagent is detectably labeled. In some embodiments of any of the aspects, the target-specific reagent is capable of generating a detectable signal. In some embodiments of any of the aspects, the target-specific reagent generates a detectable signal when the target molecule is present.

Methods to measure Chit1 gene expression products are well known to a skilled artisan. Such methods to measure gene expression products, e.g., protein level, include ELISA (enzyme linked immunosorbent assay), western blot, immunoprecipitation, and immunofluorescence using detection reagents such as an antibody or protein binding agents. Alternatively, a peptide can be detected in a subject by introducing into a subject a labeled anti-peptide antibody and other types of detection agent. For example, the antibody can be labeled with a detectable marker whose presence and location in the subject is detected by standard imaging techniques.

For example, antibodies for Chit1 are commercially available and can be used for the purposes of the invention to measure protein expression levels, e.g. anti-Chit1 (Cat. No. ab171768; Abcam, Cambridge Mass.). Alternatively, since the amino acid sequences for Chit1 are known and publically available at NCBI website, one of skill in the art can raise their own antibodies against these polypeptides of interest for the purpose of the invention.

The amino acid sequences of the polypeptides described herein, e.g. Chit1 have been assigned NCBI accession numbers for different species such as human, mouse and rat. In particular, the NCBI accession numbers for the amino acid sequence of human Chit1 is included herein, e.g. SEQ ID NO: 3 and 4.

In some embodiments of any of the aspects, immunohistochemistry ("IHC") and immunocytochemistry ("ICC") techniques can be used. IHC is the application of immunochemistry to tissue sections, whereas ICC is the application of immunochemistry to cells or tissue imprints after they have undergone specific cytological preparations such as, for example, liquid-based preparations. Immunochemistry is a family of techniques based on the use of an antibody, wherein the antibodies are used to specifically target molecules inside or on the surface of cells. The antibody typically contains a marker that will undergo a biochemical reaction, and thereby experience a change of color, upon encountering the targeted molecules. In some instances, signal amplification can be integrated into the particular protocol, wherein a secondary antibody, that includes the marker stain or marker signal, follows the application of a primary specific antibody.

In some embodiments of any of the aspects, the measurement of the level of a polypeptide can be via Western blot analysis. Alternatively, proteins can be separated by two-dimensional gel electrophoresis systems. Two-dimensional gel electrophoresis is well known in the art and typically involves iso-electric focusing along a first dimension followed by SDS-PAGE electrophoresis along a second dimension. These methods also require a considerable amount of cellular material. The analysis of 2D SDS-PAGE gels can be performed by determining the intensity of protein spots on the gel, or can be performed using immune detection. In other embodiments, protein samples are analyzed by mass spectroscopy.

Immunological tests can be used with the methods described herein and include, for example, competitive and non-competitive assay systems using techniques such as Western blots, radioimmunoassay (RIA), ELISA (enzyme linked immunosorbent assay), "sandwich" immunoassays, immunoprecipitation assays, immunodiffusion assays, agglutination assays, e.g. latex agglutination, complement-fixation assays, immunoradiometric assays, fluorescent immunoassays, e.g. FIA (fluorescence-linked immunoassay), chemiluminescence immunoassays (CLIA), electrochemiluminescence immunoassay (ECLIA, counting immunoassay (CIA), lateral flow tests or immunoassay (LFIA), magnetic immunoassay (MIA), and protein A immunoassays. Methods for performing such assays are known in the art, provided an appropriate antibody reagent is available. In some embodiments of any of the aspects, the immunoassay can be a quantitative or a semi-quantitative immunoassay.

An immunoassay is a biochemical test that measures the concentration of a substance in a biological sample, typically a fluid sample such as urine, using the interaction of an antibody or antibodies to its antigen. The assay takes advantage of the highly specific binding of an antibody with its antigen. For the methods and assays described herein, specific binding of the target polypeptides with respective proteins or protein fragments, or an isolated peptide, or a fusion protein described herein occurs in the immunoassay to form a target protein/peptide complex. The complex is then detected by a variety of methods known in the art. An immunoassay also often involves the use of a detection antibody.

Enzyme-linked immunosorbent assay, also called ELISA, enzyme immunoassay or EIA, is a biochemical technique used mainly in immunology to detect the presence of an antibody or an antigen in a sample. The ELISA has been used as a diagnostic tool in medicine and plant pathology, as well as a quality control check in various industries.

In some embodiments of any of the aspects, an ELISA involving at least one antibody with specificity for the particular desired antigen (e.g., Chit1 as described herein) can also be performed. A known amount of sample and/or antigen is immobilized on a solid support (usually a polystyrene micro titer plate). Immobilization can be either non-specific (e.g., by adsorption to the surface) or specific (e.g. where another antibody immobilized on the surface is used to capture antigen or a primary antibody). After the antigen is immobilized, the detection antibody is added, forming a complex with the antigen. The detection antibody can be covalently linked to an enzyme, or can itself be detected by a secondary antibody which is linked to an enzyme through bio-conjugation. Between each step the plate is typically washed with a mild detergent solution to remove any proteins or antibodies that are not specifically bound. After the final wash step the plate is developed by adding an enzymatic substrate to produce a visible signal, which indicates the quantity of antigen in the sample. Older ELISAs utilize chromogenic substrates, though newer assays employ fluorogenic substrates with much higher sensitivity.

In some embodiments of any of the aspects, a competitive ELISA is used. Purified antibodies that are directed against a target polypeptide or fragment thereof are coated on the solid phase of multi-well plate, i.e., conjugated to a solid surface. A second batch of purified antibodies that are not conjugated on any solid support is also needed. These non-conjugated purified antibodies are labeled for detection purposes, for example, labeled with horseradish peroxidase to produce a detectable signal. A sample (e.g., a blood sample) from a subject is mixed with a known amount of desired antigen (e.g., a known volume or concentration of a sample comprising a target polypeptide) together with the horseradish peroxidase labeled antibodies and the mixture is then are added to coated wells to form competitive combination. After incubation, if the polypeptide level is high in the sample, a complex of labeled antibody reagent-antigen will form. This complex is free in solution and can be washed away. Washing the wells will remove the complex. Then the wells are incubated with TMB (3,3',5,5'-tetramethylbenzidene) color development substrate for localization of horseradish peroxidase-conjugated antibodies in the wells. There will be no color change or little color change if the target polypeptide level is high in the sample. If there is little or no target polypeptide present in the sample, a different complex in formed, the complex of solid support bound antibody reagents-target polypeptide. This complex is immobilized on the plate and is not washed away in the wash step. Subsequent incubation with TMB will produce much color change. Such a competitive ELSA test is specific, sensitive, reproducible and easy to operate.

There are other different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; and Oellerich, M. 1984, J. Clin. Chem. Clin. Biochem. 22:895-904. These references are hereby incorporated by reference in their entirety.

In some embodiments of any of the aspects, the levels of a polypeptide in a sample can be detected by a lateral flow immunoassay test (LFIA), also known as the immunochromatographic assay, or strip test. LFIAs are a simple device intended to detect the presence (or absence) of antigen, e.g. a polypeptide, in a fluid sample. There are currently many LFIA tests are used for medical diagnostics either for home testing, point of care testing, or laboratory use. LFIA tests are a form of immunoassay in which the test sample flows along a solid substrate via capillary action. After the sample is applied to the test strip it encounters a colored reagent (generally comprising antibody specific for the test target antigen) bound to microparticles which mixes with the sample and transits the substrate encountering lines or zones which have been pretreated with another antibody or antigen. Depending upon the level of target polypeptides present in the sample the colored reagent can be captured and become bound at the test line or zone. LFIAs are essentially immunoassays adapted to operate along a single axis to suit the test strip format or a dipstick format. Strip tests are extremely versatile and can be easily modified by one skilled in the art for detecting an enormous range of antigens from fluid samples such as urine, blood, water, and/or homogenized tissue samples etc. Strip tests are also known as dip stick test, the name bearing from the literal action of "dipping" the test strip into a fluid sample to be tested. LFIA strip tests are easy to use, require minimum training and can easily be included as components of point-of-care test (POCT) diagnostics to be use on site in the field. LFIA tests can be operated as either competitive or sandwich assays. Sandwich LFIAs are similar to sandwich ELISA. The sample first encounters colored particles which are labeled with antibodies raised to the target antigen. The test line will also contain antibodies to the same target, although it may bind to a different epitope on the antigen. The test line will show as a colored band in positive samples. In some embodiments of any of the aspects, the lateral flow immunoassay can be a double antibody sandwich assay, a competitive assay, a quantitative assay or variations thereof. Competitive LFIAs are similar to competitive ELISA. The sample first encounters colored particles which are labeled with the target antigen or an analogue. The test line contains antibodies to the target/its analogue. Unlabelled antigen in the sample will block the binding sites on the antibodies preventing uptake of the colored particles. The test line will show as a colored band in negative samples. There are a number of variations on lateral flow technology. It is also possible to apply multiple capture zones to create a multiplex test.

The use of "dip sticks" or LFIA test strips and other solid supports have been described in the art in the context of an immunoassay for a number of antigen biomarkers. U.S. Pat. Nos. 4,943,522; 6,485,982; 6,187,598; 5,770,460; 5,622,871; 6,565,808, U.S. patent applications Ser. No. 10/278,676; U.S. Ser. No. 09/579,673 and U.S. Ser. No. 10/717,082, which are incorporated herein by reference in their entirety, are non-limiting examples of such lateral flow test devices. Examples of patents that describe the use of "dip stick" technology to detect soluble antigens via immunochemical assays include, but are not limited to U.S. Pat. Nos. 4,444,880; 4,305,924; and 4,135,884; which are incorporated by reference herein in their entireties. The apparatuses and methods of these three patents broadly describe a first component fixed to a solid surface on a "dip stick" which is exposed to a solution containing a soluble antigen that binds to the component fixed upon the "dip stick," prior to detection of the component-antigen complex upon the stick. It is within the skill of one in the art to modify the teachings of this "dip stick" technology for the detection of polypeptides using antibody reagents as described herein.

Other techniques can be used to detect the level of a polypeptide in a sample. One such technique is the dot blot, and adaptation of Western blotting (Towbin et at., Proc. Nat. Acad. Sci. 76:4350 (1979)). In a Western blot, the polypeptide or fragment thereof can be dissociated with detergents and heat, and separated on an SDS-PAGE gel before being transferred to a solid support, such as a nitrocellulose or PVDF membrane. The membrane is incubated with an antibody reagent specific for the target polypeptide or a fragment thereof. The membrane is then washed to remove unbound proteins and proteins with non-specific binding. Detectably labeled enzyme-linked secondary or detection antibodies can then be used to detect and assess the amount of polypeptide in the sample tested. The intensity of the signal from the detectable label corresponds to the amount of enzyme present, and therefore the amount of polypeptide. Levels can be quantified, for example by densitometry.

In some embodiments of any of the aspects, the level of, e.g., Chit1, can be measured, by way of non-limiting example, by Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluoresence assay; mass spectroscopy and/or immunoelectrophoresis assay.

In some embodiments of any of the aspects, the gene expression products as described herein can be instead determined by determining the level of messenger RNA (mRNA) expression of the genes described herein, e.g. Chit1. Such molecules can be isolated, derived, or amplified from a biological sample, such as a a blood sample. Techniques for the detection of mRNA expression is known by persons skilled in the art, and can include but not limited to, PCR procedures, RT-PCR, quantitative RT-PCR Northern blot analysis, differential gene expression, RNA protection assay, microarray based analysis, next-generation sequencing; hybridization methods, etc.

In general, the PCR procedure describes a method of gene amplification which is comprised of (i) sequence-specific hybridization of primers to specific genes or sequences within a nucleic acid sample or library, (ii) subsequent amplification involving multiple rounds of annealing, elongation, and denaturation using a thermostable DNA polymerase, and (iii) screening the PCR products for a band of the correct size. The primers used are oligonucleotides of sufficient length and appropriate sequence to provide initiation of polymerization, i.e. each primer is specifically designed to be complementary to a strand of the genomic locus to be amplified. In an alternative embodiment, mRNA level of gene expression products described herein can be determined by reverse-transcription (RT) PCR and by quantitative RT-PCR (QRT-PCR) or real-time PCR methods. Methods of RT-PCR and QRT-PCR are well known in the art.

In some embodiments of any of the aspects, the level of an mRNA can be measured by a quantitative sequencing technology, e.g. a quantitative next-generation sequence technology. Methods of sequencing a nucleic acid sequence are well known in the art. Briefly, a sample obtained from a subject can be contacted with one or more primers which specifically hybridize to a single-strand nucleic acid sequence flanking the target gene sequence and a complementary strand is synthesized. In some next-generation technologies, an adaptor (double or single-stranded) is ligated to nucleic acid molecules in the sample and synthesis proceeds from the adaptor or adaptor compatible primers. In some third-generation technologies, the sequence can be determined, e.g. by determining the location and pattern of the hybridization of probes, or measuring one or more characteristics of a single molecule as it passes through a sensor (e.g. the modulation of an electrical field as a nucleic acid molecule passes through a nanopore). Exemplary methods of sequencing include, but are not limited to, Sanger sequencing, dideoxy chain termination, high-throughput sequencing, next generation sequencing, 454 sequencing, SOLiD sequencing, polony sequencing, Illumina sequencing, Ion Torrent sequencing, sequencing by hybridization, nanopore sequencing, Helioscope sequencing, single molecule real time sequencing, RNAP sequencing, and the like. Methods and protocols for performing these sequencing methods are known in the art, see, e.g. "Next Generation Genome Sequencing" Ed. Michal Janitz, Wiley-VCH; "High-Throughput Next Generation Sequencing" Eds. Kwon and Ricke, Humanna Press, 2011; and Sambrook et al., Molecular Cloning: A Laboratory Manual (4 ed.), Cold Spring Harbor Laboratory Press, Cold Spring Harbor, N.Y., USA (2012); which are incorporated by reference herein in their entireties.

The nucleic acid sequences of the genes described herein, e.g., Chit1, have been assigned NCBI accession numbers for different species such as human, mouse and rat. For example, the human Chit1 mRNA (e.g. SEQ ID NO: 1 and 2) is known. Accordingly, a skilled artisan can design an appropriate primer based on the known sequence for determining the mRNA level of the respective gene.

Nucleic acid and ribonucleic acid (RNA) molecules can be isolated from a particular biological sample using any of a number of procedures, which are well-known in the art, the particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (Roiff, A et al. PCR: Clinical Diagnostics and Research, Springer (1994)).

In some embodiments of any of the aspects, one or more of the reagents (e.g. an antibody reagent and/or nucleic acid probe) described herein can comprise a detectable label and/or comprise the ability to generate a detectable signal (e.g. by catalyzing reaction converting a compound to a detectable product). Detectable labels can comprise, for example, a light-absorbing dye, a fluorescent dye, or a radioactive label. Detectable labels, methods of detecting them, and methods of incorporating them into reagents (e.g. antibodies and nucleic acid probes) are well known in the art.

In some embodiments of any of the aspects, detectable labels can include labels that can be detected by spectroscopic, photochemical, biochemical, immunochemical, electromagnetic, radiochemical, or chemical means, such as fluorescence, chemifluoresence, or chemiluminescence, or any other appropriate means. The detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies). The detectable label can be linked by covalent or non-covalent means to the reagent. Alternatively, a detectable label can be linked such as by directly labeling a molecule that achieves binding to the reagent via a ligand-receptor binding pair arrangement or other such specific recognition molecules. Detectable labels can include, but are not limited to radioisotopes, bioluminescent compounds, chromophores, antibodies, chemiluminescent compounds, fluorescent compounds, metal chelates, and enzymes.

In other embodiments, the detection reagent is label with a fluorescent compound. When the fluorescently labeled reagent is exposed to light of the proper wavelength, its presence can then be detected due to fluorescence. In some embodiments of any of the aspects, a detectable label can be a fluorescent dye molecule, or fluorophore including, but not limited to fluorescein, phycoerythrin, phycocyanin, o-phthaldehyde, fluorescamine, Cy3™, Cy5™, allophycocyanine, Texas Red, peridenin chlorophyll, cyanine, tandem conjugates such as phycoerythrin-Cy5™, green fluorescent protein, rhodamine, fluorescein isothiocyanate (FITC) and Oregon Green, rhodamine and derivatives (e.g., Texas red and tetrarhodimine isothiocynate (TRITC)), biotin, phycoerythrin, AMCA, CyDyes™, 6-carboxyfhiorescein (commonly known by the abbreviations FAM and F), 6-carboxy-2',4',7',4,7-hexachlorofiuorescein (HEX), 6-carboxy-4',5'-dichloro-2',7'-dimethoxyfiuorescein (JOE or J), N,N,N',N'-tetramethyl-6carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. In some embodiments of any of the aspects, a detectable label can be a radiolabel including, but not limited to $^3H$, $^{125}I$, $^{35}S$, $^{14}C$, $^{32}P$, and $^{33}P$. In some embodiments of any of the aspects, a detectable label can be an enzyme including, but not limited to horseradish peroxidase and alkaline phosphatase. An enzymatic label can produce, for example, a chemiluminescent signal, a color signal, or a fluorescent signal. Enzymes contemplated for use to detectably label an antibody reagent include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase. In some embodiments of any of the aspects, a detectable label is a chemiluminescent label, including, but not limited to lucigenin, luminol, luciferin, isoluminol, theromatic acridinium ester, imidazole, acridinium salt and oxalate ester. In some embodiments of any of the aspects, a detectable label can be a spectral colorimetric label including, but not limited to colloidal gold or colored glass or plastic (e.g., polystyrene, polypropylene, and latex) beads.

In some embodiments of any of the aspects, detection reagents can also be labeled with a detectable tag, such as c-Myc, HA, VSV-G, HSV, FLAG, V5, HIS, or biotin. Other detection systems can also be used, for example, a biotin-streptavidin system. In this system, the antibodies immunoreactive (i. e. specific for) with the biomarker of interest is biotinylated. Quantity of biotinylated antibody bound to the biomarker is determined using a streptavidin-peroxidase conjugate and a chromagenic substrate. Such streptavidin peroxidase detection kits are commercially available, e.g. from DAKO; Carpinteria, Calif. A reagent can also be detectably labeled using fluorescence emitting metals such as $^{152}Eu$, or others of the lanthanide series. These metals can be attached to the reagent using such metal chelating groups as diethylenetriaminepentaacetic acid (DTPA) or ethylenediaminetetraacetic acid (EDTA).

A level which is greater than a reference level can be a level which is greater by at least about 10%, at least about 20%, at least about 50%, at least about 100%, at least about 200%, at least about 300%, at least about 500%, at least about 1000%, or greater than the reference level. In some embodiments of any of the aspects, a level which is greater than a reference level can be a level which is statistically significantly greater than the reference level. In some embodiments of any of the aspects, the reference can be a level of Chit1 in a population of subjects who do not have or are not diagnosed as having, and/or do not exhibit signs or symptoms of a fibrotic disease. In some embodiments of any of the aspects, the reference can also be a level of expression of Chit1 in a control sample, a pooled sample of control individuals or a numeric value or range of values based on the same. In some embodiments of any of the aspects, the reference can be the level of Chit1 in a sample obtained from the same subject at an earlier point in time.

In some embodiments of any of the aspects, the level of expression products of no more than 200 other genes is determined. In some embodiments of any of the aspects, the level of expression products of no more than 100 other genes is determined. In some embodiments of any of the aspects, the level of expression products of no more than 20 other genes is determined. In some embodiments of any of the aspects, the level of expression products of no more than 10 other genes is determined.

In some embodiments of the foregoing aspects, the expression level of a given gene, e.g., Chit1, can be normalized relative to the expression level of one or more reference genes or reference proteins.

The term "sample" or "test sample" as used herein denotes a sample taken or isolated from a biological organism, e.g., a blood or plasma sample from a subject. Exemplary biological samples include, but are not limited to, a biofluid sample; serum; plasma; urine; saliva; and/or tissue sample etc. The term also includes a mixture of the above-mentioned samples. The term "test sample" also includes untreated or pretreated (or pre-processed) biological samples. In some embodiments of any of the aspects, a test sample can comprise cells from subject. In some embodiments of any of the aspects, the test sample can be a blood sample. In some embodiments of any of the aspects, the test sample can be a plasma sample.

The test sample can be obtained by removing a sample from a subject, but can also be accomplished by using previously sample (e.g. isolated at a prior timepoint and isolated by the same or another person). In addition, the test sample can be freshly collected or a previously collected sample.

In some embodiments of any of the aspects, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments of any of the aspects, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments of any of the aspects, the test sample is a clarified test sample, for example, by centrifugation and collection of a supernatant comprising the clarified test sample. In some embodiments of any of the aspects, a test sample can be a pre-processed test sample, for example, supernatant or filtrate resulting from a treatment selected from the group consisting of centrifugation, filtration, thawing, purification, and any combinations thereof. In some embodiments of any of the aspects, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for determination of the level of an expression product as described herein.

In some embodiments of any of the aspects, the methods, assays, and systems described herein can further comprise a step of obtaining a test sample from a subject. In some embodiments of any of the aspects, the subject can be a human subject. In some embodiments of any of the aspects, the subject can be a subject in need of treatment for (e.g. having or diagnosed as having) a fibrotic disease.

In some embodiments of any of the aspects, the methods described herein relate to treating a subject having or diagnosed as having a fibrotic disease with kasugamycin or a derivative, analog, or variant thereof. Subjects having a fibrotic disease, e.g., pulmonary fibrosis can be identified by a physician using current methods of diagnosing pulmonary fibrosis. Symptoms and/or complications of pulmonary fibrosis which characterize these conditions and aid in diagnosis are well known in the art and include but are not limited to, shortness of breath, a dry hacking cough, fast shallow breathing, gradual unintended weight loss, and tiredness. Tests that may aid in a diagnosis of, e.g. pulmonary fibrosis include, but are not limited to, chest x-ray, breathing tests, exercise tests, lung biopsy, blood tests, and high resolution CT scan. A family history of pulmonary fibrosis, or exposure to risk factors for pulmonary fibrosis (e.g. cigarette smoke, certain viral infections, exposure to certain chemicals or toxins) can also aid in determining if a subject is likely to have pulmonary fibrosis or in making a diagnosis of pulmonary fibrosis.

The compositions and methods described herein can be administered to a subject having or diagnosed as having a fibrotic disease. In some embodiments of any of the aspects, the methods described herein comprise administering an effective amount of compositions described herein, e.g. kasugamycin or a derivative, analog, or variant thereof to a subject in order to alleviate a symptom of a fibrotic disease. As used herein, "alleviating a symptom" is ameliorating any condition or symptom associated with the disease. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, or injection, administration. Administration can be local or systemic. In some embodiments of any of the aspects, the kasugamycin or derivative thereof is administered directly to a site of fibrosis.

The term "effective amount" as used herein refers to the amount of kasugamycin or a derivative, analog, or variant thereof needed to alleviate at least one or more symptom of the disease or disorder, and relates to a sufficient amount of pharmacological composition to provide the desired effect. The term "therapeutically effective amount" therefore refers to an amount of kasugamycin or a derivative, analog, or variant thereof that is sufficient to provide a particular effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the active ingredient, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for collagen formation and/or chitinase activity, among others. The dosage can be determined by a physician and adjusted, as necessary, to suit observed effects of the treatment.

In some embodiments of any of the aspects, the technology described herein relates to a pharmaceutical composition comprising kasugamycin or a derivative, analog, or variant thereof as described herein, and optionally a pharmaceutically acceptable carrier. In some embodiments of any of the aspects, the active ingredients of the pharmaceutical composition comprise kasugamycin or a derivative, analog, or variant thereof as described herein. In some embodiments of any of the aspects, the active ingredients of the pharmaceutical composition consist essentially of kasugamycin or a derivative, analog, or variant thereof as described herein. In some embodiments of any of the aspects, the active ingredients of the pharmaceutical composition consist of kasugamycin or a derivative, analog, or variant thereof as described herein. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments of any of the aspects, the carrier inhibits the degradation of the active agent, e.g. kasugamycin or a derivative, analog, or variant thereof as described herein.

In some embodiments of any of the aspects, the pharmaceutical composition comprising kasugamycin or a derivative, analog, or variant thereof as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of kasugamycin or a derivative, analog, or variant thereof as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of kasugamycin or a derivative, analog, or variant thereof as disclosed herein can also be incorporated into the parenteral dosage forms of the disclosure, including conventional and controlled-release parenteral dosage forms.

Pharmaceutical compositions comprising kasugamycin or a derivative, analog, or variant thereof can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments of any of the aspects, the kasugamycin or a derivative, analog, or variant thereof can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

Im some embodiments of any of the apsects, the kasugamycin or a derivative, analog, or variant thereof described herein is administered as a monotherapy, e.g., another treatment for the fibrosis and/or fibrotic disease is not administered to the subject.

In some emboidments of any of the aspects, the methods described herein can further comprise administering a second agent and/or treatment to the subject, e.g. as part of a combinatorial therapy.

In some embodiments of any of the aspects, an effective dose of a composition comprising kasugamycin or a derivative, analog, or variant thereof as described herein can be administered to a patient once. In some embodiments of any of the aspects, an effective dose of a composition comprising kasugamycin or a derivative, analog, or variant thereof can be administered to a patient repeatedly. For systemic administration, subjects can be administered a therapeutic amount of a composition comprising kasugamycin or a derivative, analog, or variant thereof, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments of any of the aspects, the kasugamycin or a derivative, analog, or variant thereof as described herein can be administered at a dose of more than about 50 mg/kg. In some embodiments of any of the aspects, the kasugamycin or a derivative, analog, or variant thereof as described herein can be administered at a dose of about 100 mg/kg or greater. In some embodiments of any of the aspects, the kasugamycin or a derivative, analog, or variant thereof as described herein can be administered at a dose from about 50 mg/kg to about 500 mg/kg. In some embodiments of any of the aspects, the kasugamycin or a derivative, analog, or variant thereof as described herein can be administered at a dose from about 50 mg/kg to about 1,000 mg/kg. In some embodiments of any of the aspects, the kasugamycin or a derivative, analog, or variant thereof as described herein can be administered at a dose from about 100 mg/kg to about 500 mg/kg.

In some embodiments of any of the aspects, the kasugamycin or a derivative, analog, or variant thereof as described herein can be administered at a dose of more than 50 mg/kg. In some embodiments of any of the aspects, the kasugamycin or a derivative, analog, or variant thereof as described herein can be administered at a dose of 100 mg/kg or greater. In some embodiments of any of the aspects, the kasugamycin or a derivative, analog, or variant thereof as described herein can be administered at a dose from 50 mg/kg to 500 mg/kg. In some embodiments of any of the aspects, the kasugamycin or a derivative, analog, or variant thereof as described herein can be administered at a dose from 50 mg/kg to 1,000 mg/kg. In some embodiments of any of the aspects, the kasugamycin or a derivative, analog, or variant thereof as described herein can be administered at a dose from 100 mg/kg to 500 mg/kg.

In some embodiments of any of the aspects, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. kasugamycin or a derivative, analog, or variant thereof by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to kasugamycin or a derivative, analog, or variant thereof. The desired dose or amount of activation can be administered at one time or divided into subdoses, e.g., 2-4 subdoses and administered over a period of time, e.g., at appropriate intervals through the day or other appropriate schedule. In some embodiments of any of the aspects, administration can be chronic, e.g., one or more doses and/or treatments daily over a period of weeks or months.

Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition comprising kasugamycin or a derivative, analog, or variant thereof can be administered over a period of time, such as over a 5 minute, 10 minute, 15 minute, 20 minute, or 25 minute period.

The dosage ranges for the administration of kasugamycin or a derivative, analog, or variant thereof, according to the methods described herein depend upon, for example, the form of the active ingredient, its potency, and the extent to which symptoms, markers, or indicators of a condition described herein are desired to be reduced, for example the percentage reduction desired for fibrosis. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of kasugamycin or a derivative, analog, or variant thereof in, e.g. the treatment of a condition described herein, or to induce a response as described herein (e.g. a decrease of chitinase activity) can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. chitinase activity. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response, (e.g. collagen levels, degree of fibrosis, and/or BAL cell recovery). It is well within the ability of one skilled in the art to monitor efficacy of administration and/or treatment by measuring any one of such parameters, or any combination of parameters. Efficacy can be assessed in animal models of a condition described herein, for example treatment of mouse models of pulmonary fibrosis. When using an experimental animal model, efficacy of treatment is evidenced when a statistically significant change in a marker is observed, e.g. collagen levels, and/or chitinase activity.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments of any of the aspects, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments of any of the aspects, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments of any of the aspects, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of fibrosis. A subject can be male or female.

A subject can be one who has been previously diagnosed with or identified as suffering from or having a condition in need of treatment (e.g. a fibrotic disease) or one or more complications related to such a condition, and optionally, have already undergone treatment for the condition or the one or more complications related to the condition. Alternatively, a subject can also be one who has not been previously diagnosed as having the condition or one or more complications related to the condition. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

In some embodiments of any of the aspects, the polypeptide described herein can be a variant of a sequence described herein. In some embodiments of any of the aspects, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are known in the art and can be applied by the ordinarily skilled artisan.

A variant amino acid or DNA sequence can be at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA or cDNA. Suitable RNA can include, e.g., mRNA.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. a fibrotic disease. The term "treating" includes reducing or alleviating at least one adverse effect or symptom of a condition, disease or disorder associated with a fibrotic disease. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in in nature.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, $4^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, func- Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method of treating a fibrotic disease in a subject in need thereof, the method comprising administering kasugamycin or derivatives thereof to the subject.
2. The method of paragraph 1, wherein the method comprises administering kasugamycin.
3. The method of any of paragraphs 1-2, wherein the morbidity and mortality of the disease is characterized by tissue fibrosis.
4. The method of any of paragraphs 1-3, wherein the fibrotic disease is characterized by etiological fibrosis.
5. The method of any of paragraphs 1-4, wherein the fibrotic disease is not cystic fibrosis.
6. The method of any of paragraphs 1-5, wherein the fibrotic disease is pulmonary fibrosis.
7. The method of any of paragraphs 1-6, wherein the fibrotic disease is associated with abnormalities in Chitinase 1 (Chit1) and or a Chit1-mediated fibrotic disease.
8. The method of any of paragraphs 1-7, wherein the fibrotic disease is selected from the group consisting of: idiopathic pulmonary fibrosis; scleroderma; scleroderma of the skin; scleroderma of the lungs; a collagen vascular disease; lupus; rheumatoid arthritis; scleroderma; genetic pulmonary fibrosis; Hermansky-Pudlak Syndrome; radiation pneumonitis; asthma; asthma with airway remodeling; chemotherapy-induced pulmonary fibrosis; radiation fibrosis; Gaucher's disease; interstitial lung disease; retroperitoneal fibrosis; myelofibrosis; interstitial or pulmonary vascular disease; fibrosis or interstitial lung disease associated with drug exposure; interstitial lung disease associated with exposures such as asbestosis, silicosis, and grain exposure; and chronic hypersensitivity pneumonitis.
9. The method of any of paragraphs 1-8, wherein the subject has been determined to have an increased level of Chit1 and/or Chit1 activity.

Some embodiments of the technology described herein can be defined according to any of the following numbered paragraphs:

1. A method of treating a fibrotic disease in a subject in need thereof, the method comprising administering kasugamycin or derivatives thereof to the subject.
2. The method of paragraph 1, wherein the method comprises administering kasugamycin.
3. The method of any of paragraphs 1-2, wherein the kasugamycin or derivative thereof is administered orally.
4. The method of any of paragraphs 1-3, wherein the morbidity and mortality of the disease is characterized by tissue fibrosis.
5. The method of any of paragraphs 1-4, wherein the fibrotic disease is characterized by etiological fibrosis.
6. The method of any of paragraphs 1-5, wherein the fibrotic disease is not cystic fibrosis.
7. The method of any of paragraphs 1-6, wherein the fibrotic disease is pulmonary fibrosis.
8. The method of any of paragraphs 1-7, wherein the fibrotic disease is associated with abnormalities in Chitinase 1 (Chit1) and/or is a Chit1-mediated fibrotic disease.
9. The method of any of paragraphs 1-8, wherein the fibrotic disease is associated with abnormalities in Transforming Growth Factor Beta 1 (TGFβ1) and/or is a TGFβ1-associated fibrotic disease.
10. The method of any of paragraphs 1-9, wherein the fibrotic disease is selected from the group consisting of: idiopathic pulmonary fibrosis; scleroderma; scleroderma of the skin; scleroderma of the lungs; a collagen vascular disease; lupus; rheumatoid arthritis; scleroderma; genetic pulmonary fibrosis; Hermansky-Pudlak Syndrome; radiation pneumonitis; asthma; asthma with airway remodeling; chemotherapy-induced pulmonary fibrosis; radiation fibrosis; Gaucher's disease; interstitial lung disease; retroperitoneal fibrosis; myelofibrosis; interstitial or pulmonary vascular disease; fibrosis or interstitial lung disease associated with drug exposure; interstitial lung disease associated with exposures such as asbestosis, silicosis, and grain exposure; chronic hypersensitivity pneumonitis; an adhesion; an intestinal or abdominal adhesion; cardiac fibrosis; kidney fibrosis; cirrhosis; and nonalcoholic steastohepatitis (NASH)-induced fibrosis.
11. The method of any of paragraphs 1-10, wherein the subject has been determined to have an increased level of Chit1 and/or Chit1 activity.
12. A composition comprising kasugamycin and/or a derivative thereof for use in a method of treating a fibrotic disease.
13. The composition of paragraph 12, wherein the composition comprises kasugamycin.
14. The composition of any of paragraphs 12-13, wherein the composition is administered orally.
15. The composition of any of paragraphs 12-14, wherein the morbidity and mortality of the disease is characterized by tissue fibrosis.
16. The composition of any of paragraphs 12-15, wherein the fibrotic disease is characterized by etiological fibrosis.
17. The composition of any of paragraphs 12-16, wherein the fibrotic disease is not cystic fibrosis.
18. The composition of any of paragraphs 12-17, wherein the fibrotic disease is pulmonary fibrosis.
19. The composition of any of paragraphs 12-18, wherein the fibrotic disease is associated with abnormalities in Chitinase 1 (Chit1) and/or is a Chit1-mediated fibrotic disease.
20. The composition of any of paragraphs 12-19, wherein the fibrotic disease is associated with abnormalities in Transforming Growth Factor Beta 1 (TGFβ1) and/or is a TGFβ1-associated fibrotic disease.

21. The composition of any of paragraphs 12-20, wherein the fibrotic disease is selected from the group consisting of:
    idiopathic pulmonary fibrosis; scleroderma; scleroderma of the skin; scleroderma of the lungs; a collagen vascular disease; lupus; rheumatoid arthritis; scleroderma; genetic pulmonary fibrosis; Hermansky-Pudlak Syndrome; radiation pneumonitis; asthma; asthma with airway remodeling; chemotherapy-induced pulmonary fibrosis; radiation fibrosis; Gaucher's disease; interstitial lung disease; retroperitoneal fibrosis; myelofibrosis; interstitial or pulmonary vascular disease; fibrosis or interstitial lung disease associated with drug exposure; interstitial lung disease associated with exposures such as asbestosis, silicosis, and grain exposure; chronic hypersensitivity pneumonitis; an adhesion; an intestinal or abdominal adhesion; cardiac fibrosis; kidney fibrosis; cirrhosis; and nonalcoholic steastohepatitis (NASH)-induced fibrosis.
22. The composition of any of paragraphs 12-21, wherein the subject has been determined to have an increased level of Chit1 and/or Chit1 activity.

EXAMPLES

Example 1

Chit1 is a biomarker and therapeutic target of SSc-ILD, as well as plahing a significant role in bleomycin- and IL-13-induced pulmonary fibrosis. In order to discover new therapeutic approaches for fibrotic diseases, we screened for inhibitors of Chit1, using pentoxifylline as a positive control. The results of the screen were expressed as a % of the inhibitory activity of 200 uM of pentoxifylline. This assay identified 51 compounds that have more than 45% of inhibition (compared to 200 μM pentoxifylline). One of the compounds so identified was kasugamycin.

Figure 4:
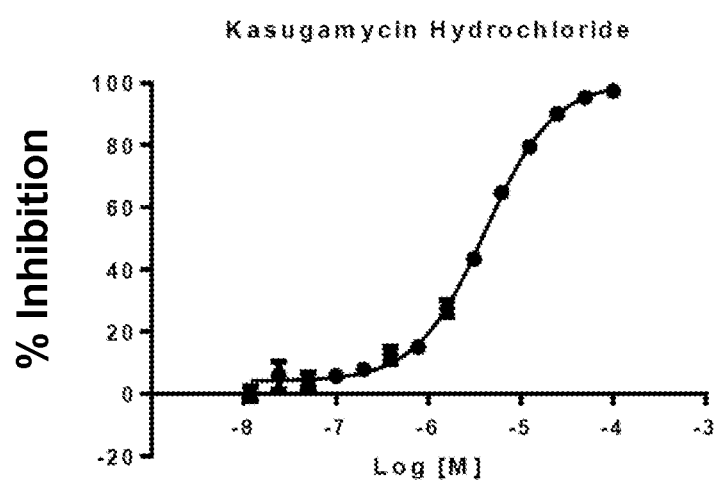
FIG. 4 depicts dose-response validation of inhibitory activities of kasuagmycin on Chit1 activities
Figure 5:
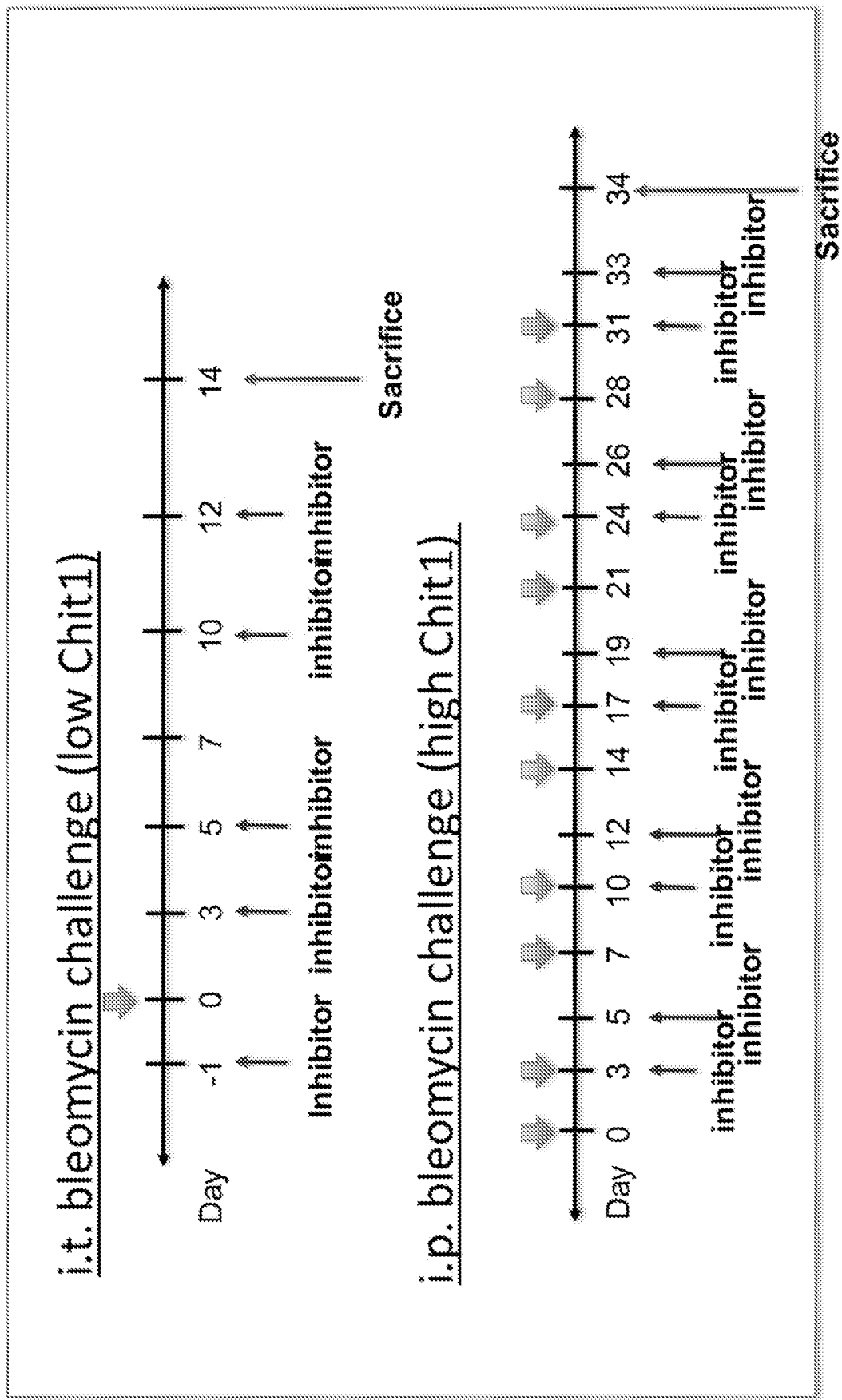
FIG. 5 depicts schematic diagrams of in vivo validation of antifibrotic effect of Chit1 inhibitors using bleomycin models of pulmonary fibrosis
Figure 6:
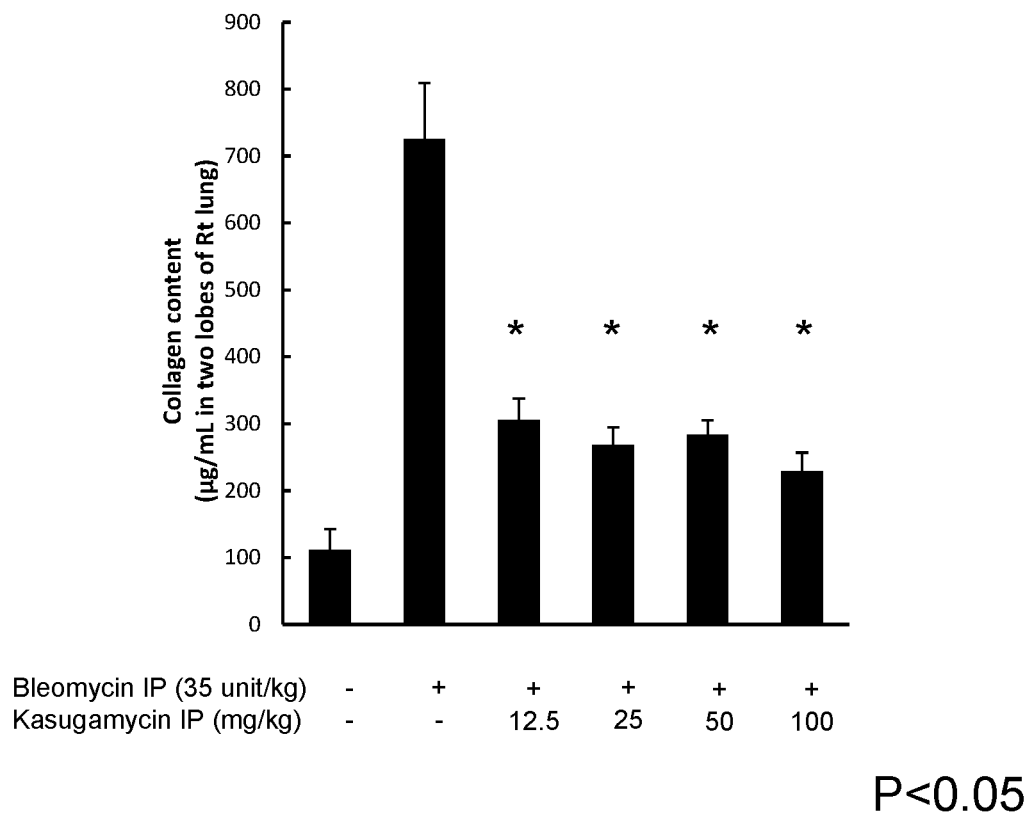
FIG. 6 depicts a graph of total lung collagen with and without Kasugamycin treatment (I.P. Model)
Figure 7:
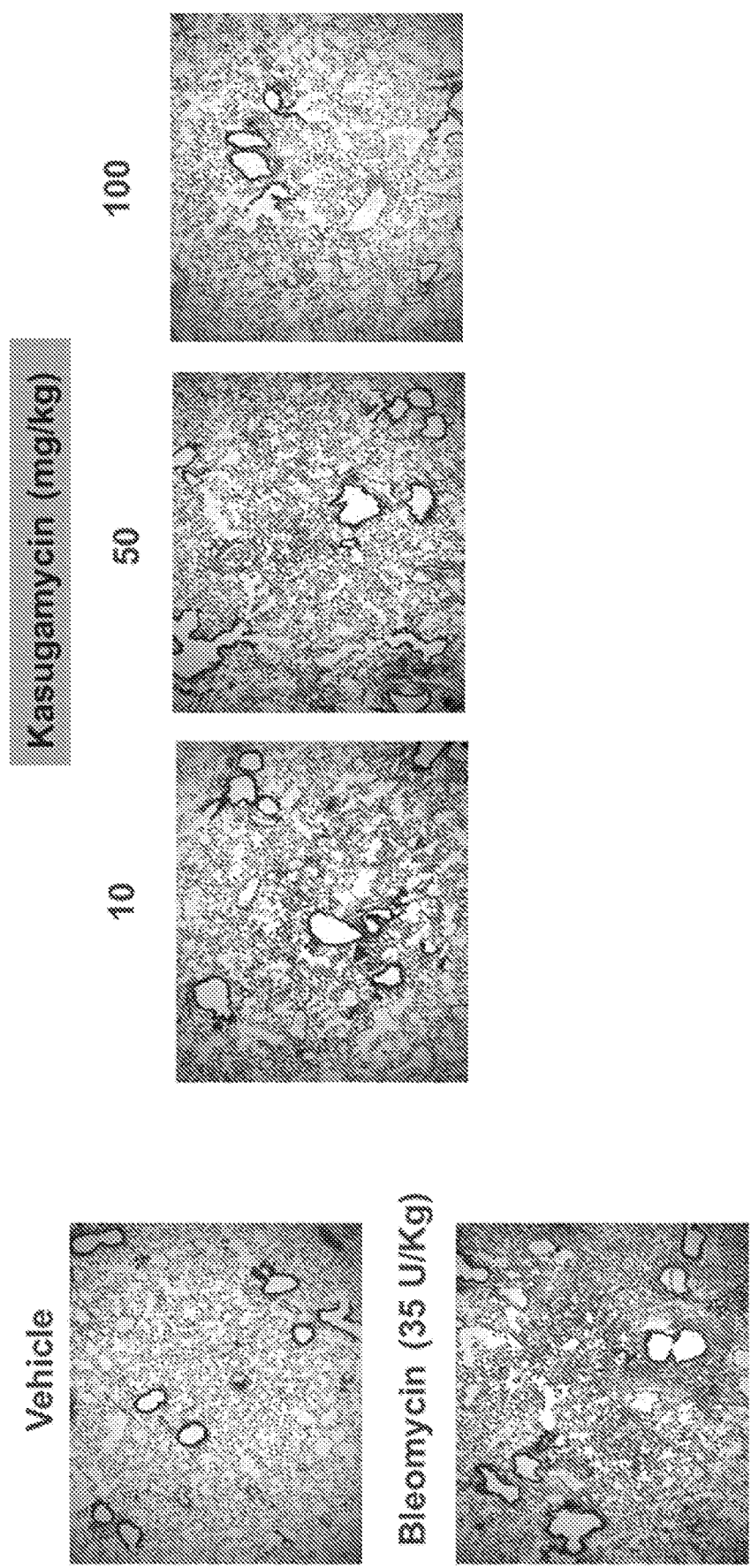
FIG. 7 depicts representative lung histology with and without Chit1 inhibitor (Kasugamycin) treatment (I.P. Model)
Figure 8:
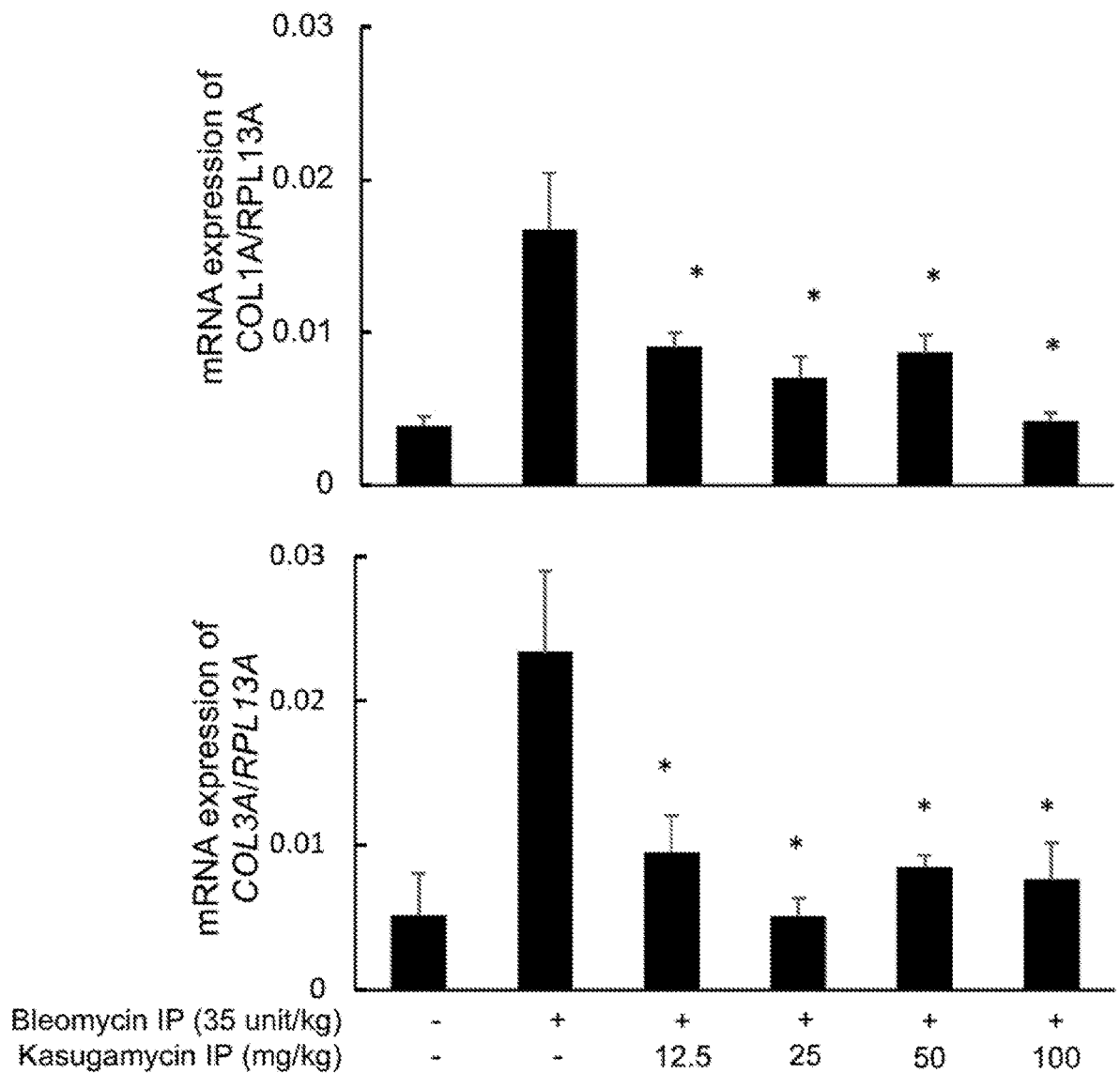
FIG. 8 depicts lung collagen expression with and without Kasugamycin treatment (I.P. Model)
Figure 9:
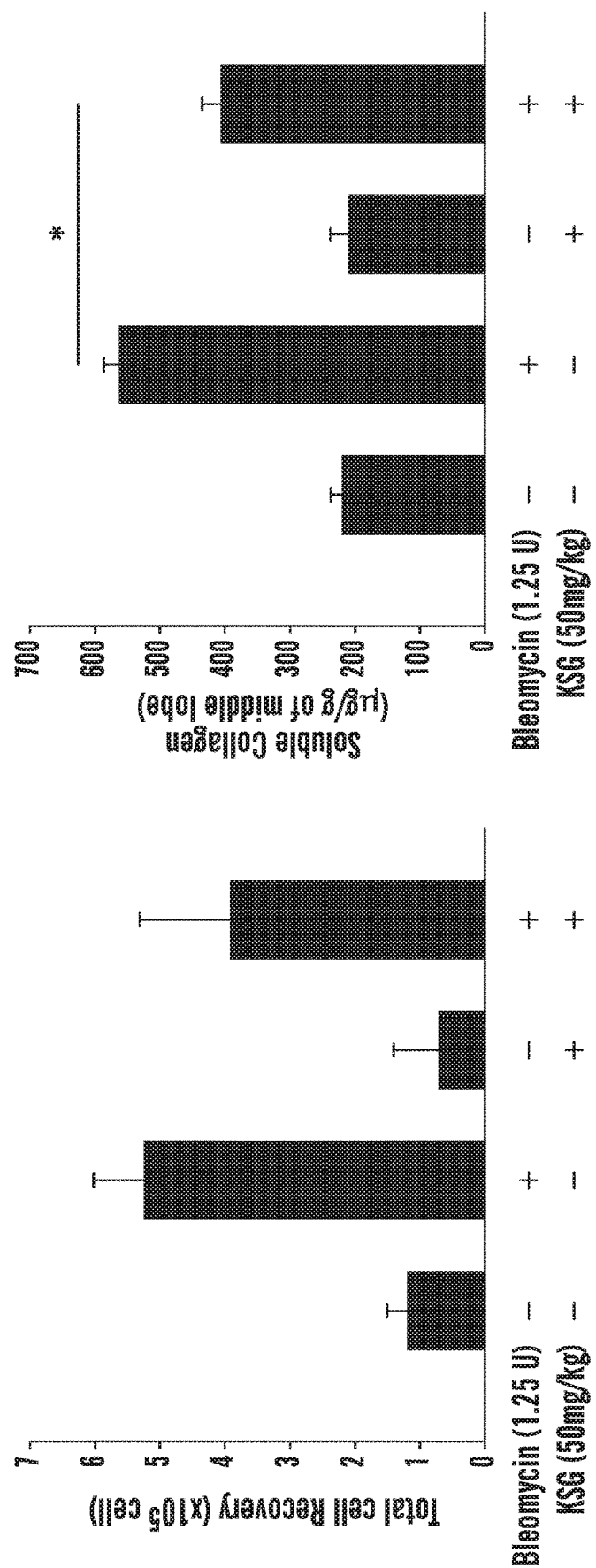
FIG. 9 depicts BAL cell recovery and total lung coallagen with and without Kasugamycin treatment (I.T. Model)
Figure 10:
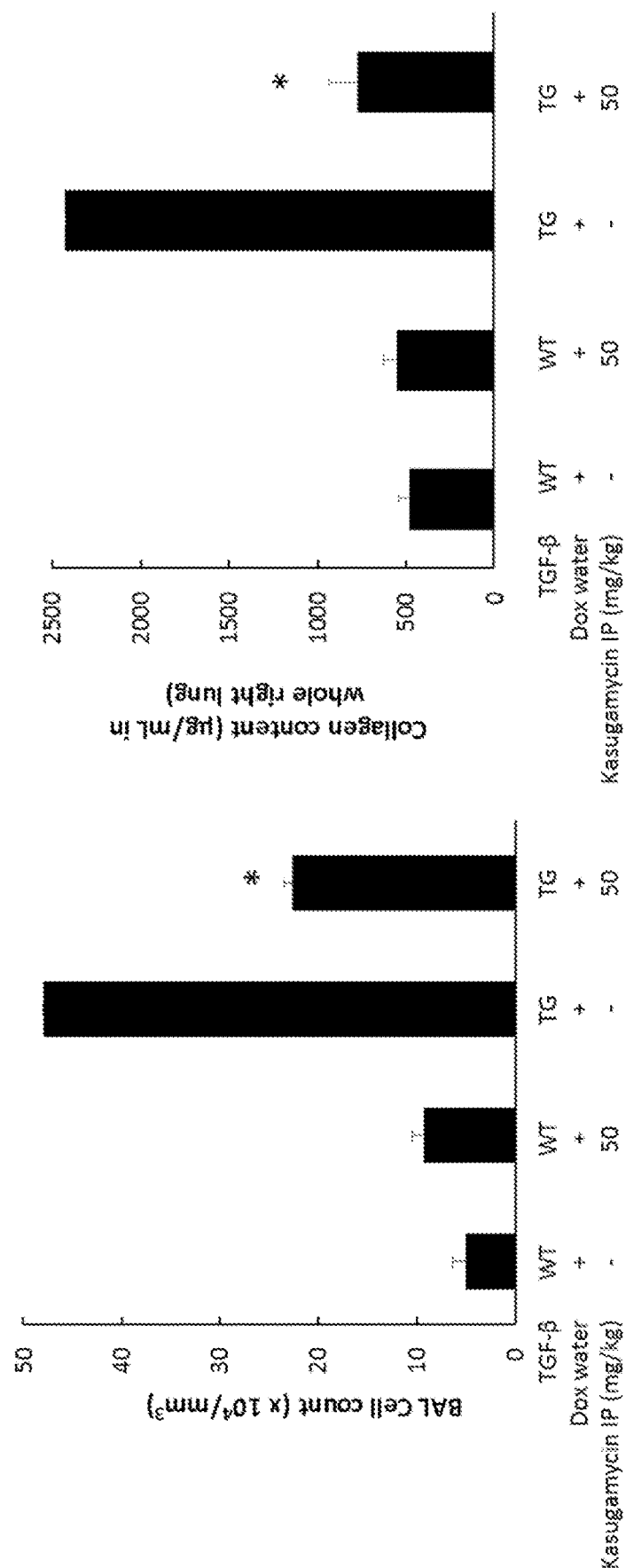
FIG. 10 depicts graphs of the effect of Kasugamycin on transgenic TGFβ1-stimulated inflammation and fibrosis
Figure 11:
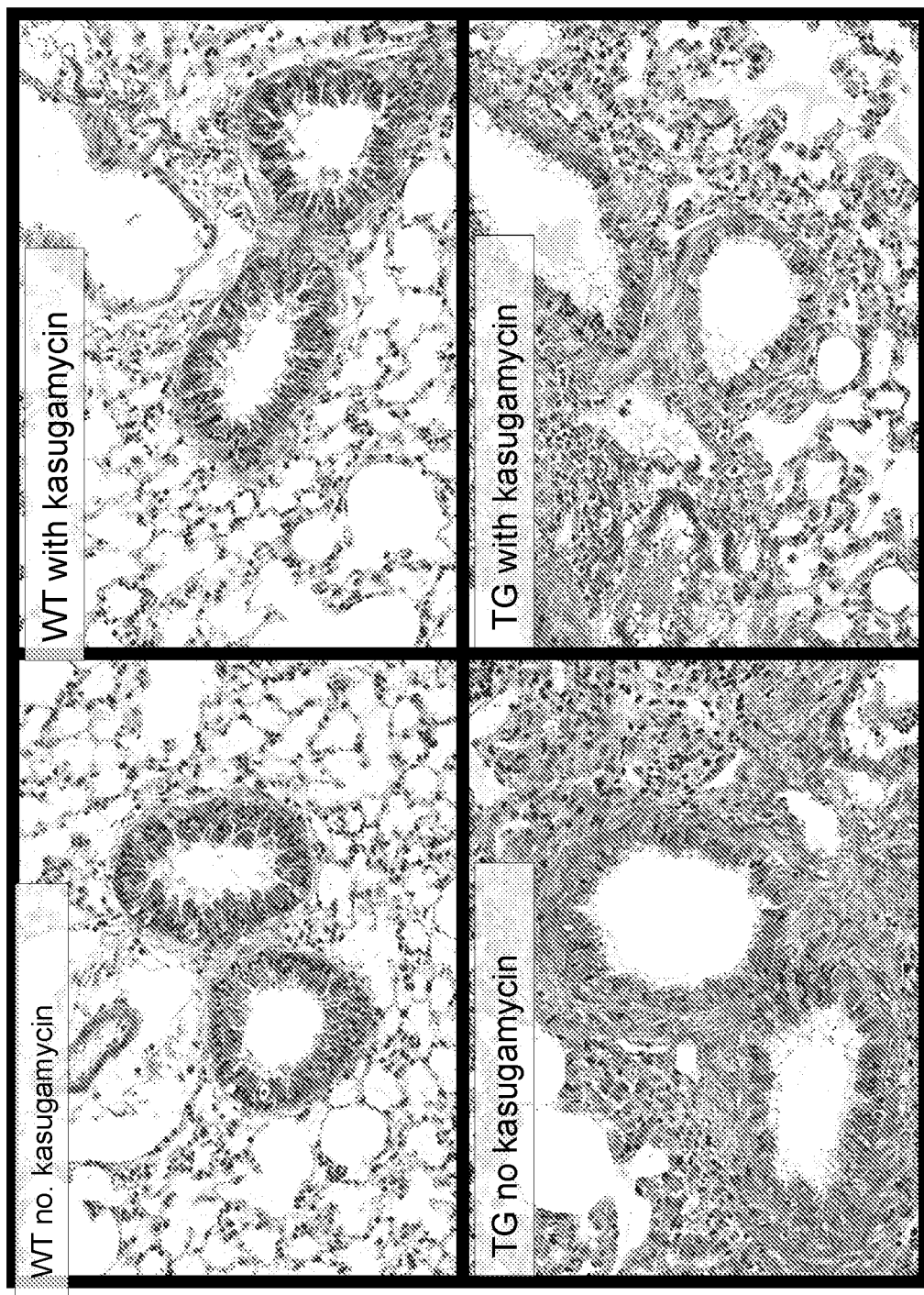
FIG. 11 depicts the effect of kasugamycin on TGFβ1-stimulated fibrosis. In this figure WT=wild type mice; TG=TGFβ1 transgenic mice.

The results were validated by measuring dose-response (FIG. 4). Assay conditions were 0.33 nM of recombinant Chit1, 1 μM of test compound, 4 μM of substrate, 30 min incubation at room temperature. In vivo validation (FIG. 5) was also conducted, demonstrating the reduction of collagen (FIG. 6, 8) and affect on histology (FIG. 7) of kasugamycin. In the I.T. model, kasugamycin also reduced lung collagen and affected BAL cell recovery (FIG. 9). Kasuagmyicn also inhibited inflammation and fibrosis in response to transgenic TGFβ1 stimulation (FIG. 10, FIG. 11).

Example 2

Figure 2:
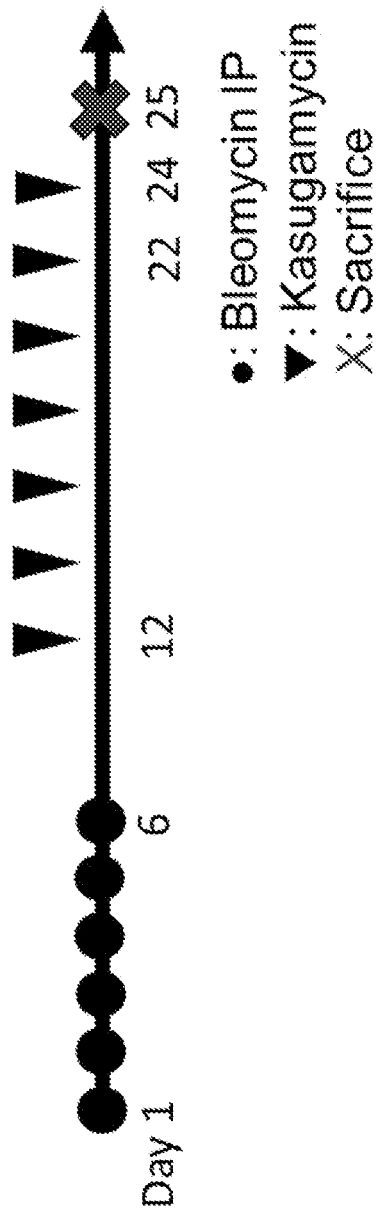
FIG. 2 depicts a schematic of experiments described herein, using a method reported by Inomata et al (Respiratory Research, 2014, 15:16) that was used for therapeutic efficacy of pirifenidone with minor modification. 8 Week old C57 BL/6 mice were used for the evaluation. Bleomycin (25 Unit/kg) was given daily for 6 days. Seven days after the last bleomycin challenge, Kasugamycin (50 mg/Kg) or PBS were delivered every other day via I.P. injection. The mice received a total of 7 doses of Kasugamycin. The mice were sacrificed a day after the last injection of Kasugamycin.
Figure 3A:
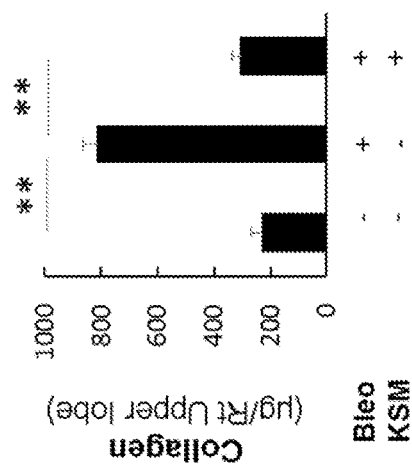
FIGS. 3A-3B demonstrate that kasugamycin reduced pulmonary fibrosis after bleomycin.
Figure 3B:
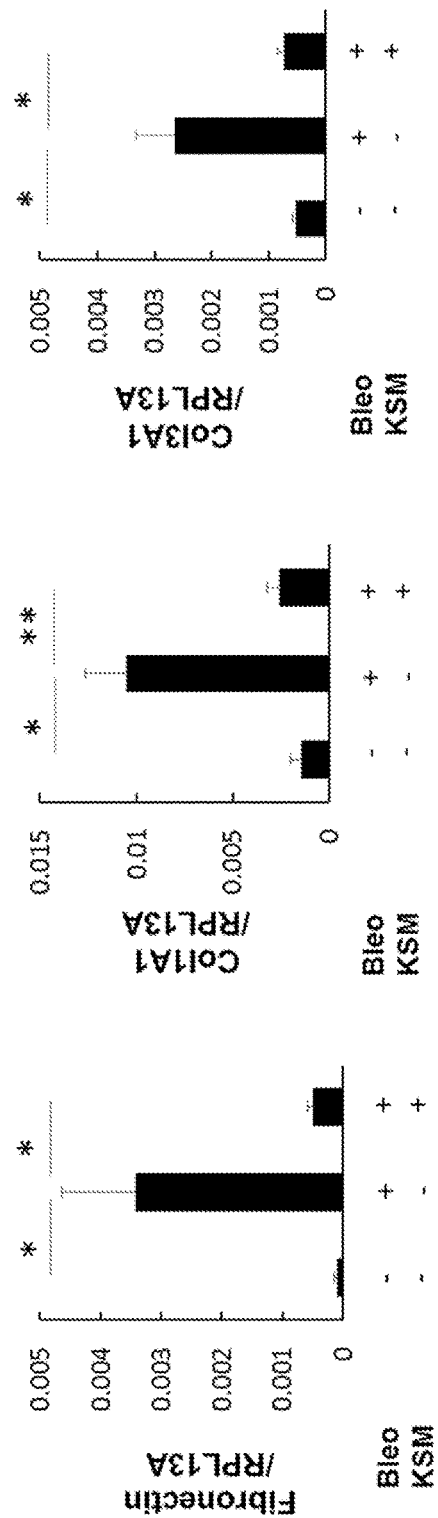

The therapeutic window of kasugamycin was investigated using the method described in Inomata et al (Respiratory Research 2014 15:16) that was used to establish the therapeutic efficacy of pirifendidone, with minor modifications. Briefly, 8 week old C57 BL/6 mice were used for the evaluation. Bleomycin (25 Unit/kg) was given daily for 6 days. Seven days after the last bleomycin challenge, kasugamycin (50 mg/Kg) or PBS were delivered every other day via I.P. injection. The mice received a total of 7 doses of kasugamycin. The mice were sacrificed a day after the last injection of kasugamycin (FIG. 2).

Figure 12A:
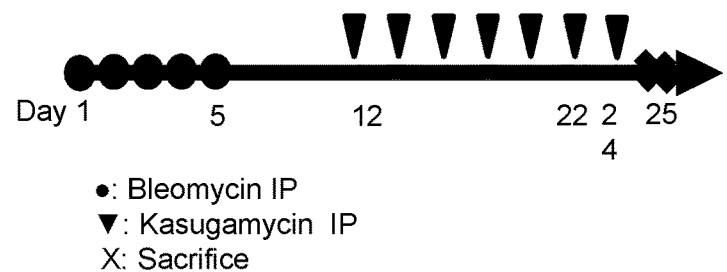
FIGS. 12A-12B demonstrate the effects of kasugamycin in bleomycin-treated Hermansky-Pudlak syndrome mice.
Figure 12B:
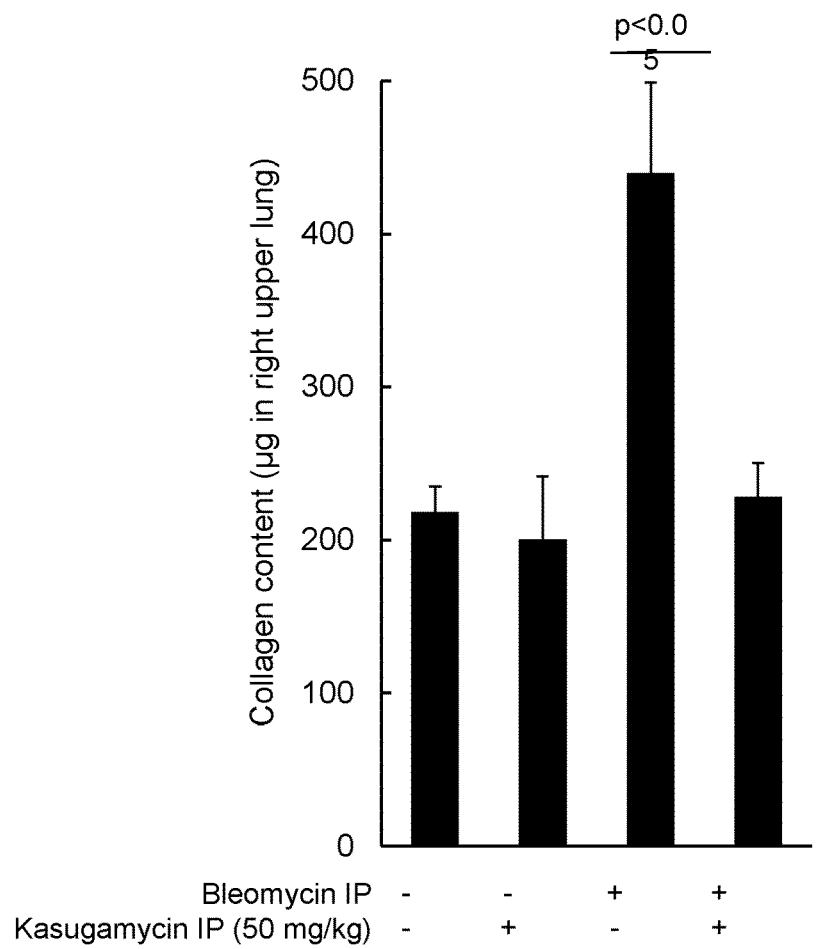
Figure 13A:
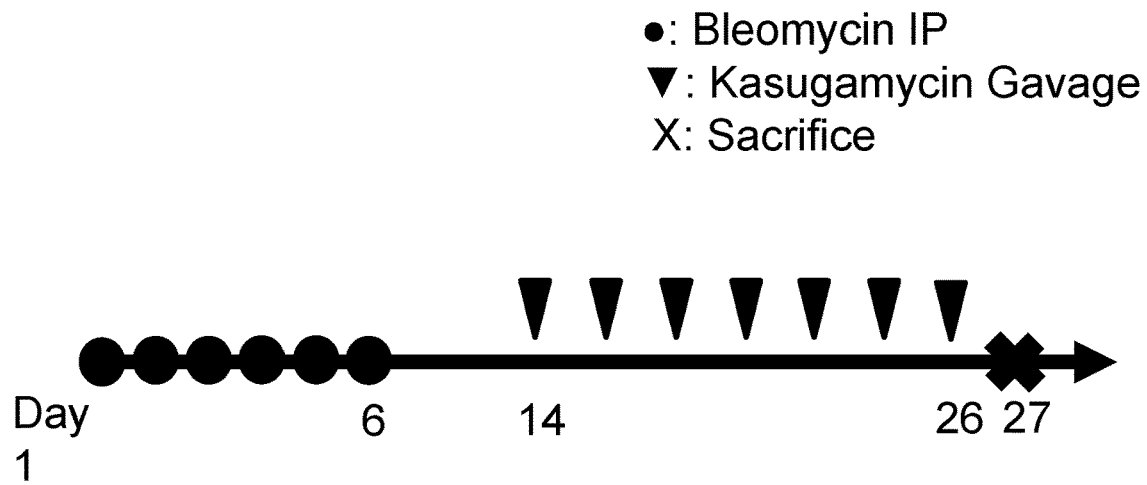
FIGS. 13A-13B depict the effect of kasugamycin when given by gavage in the bleomycin IP model.
Figure 13B:
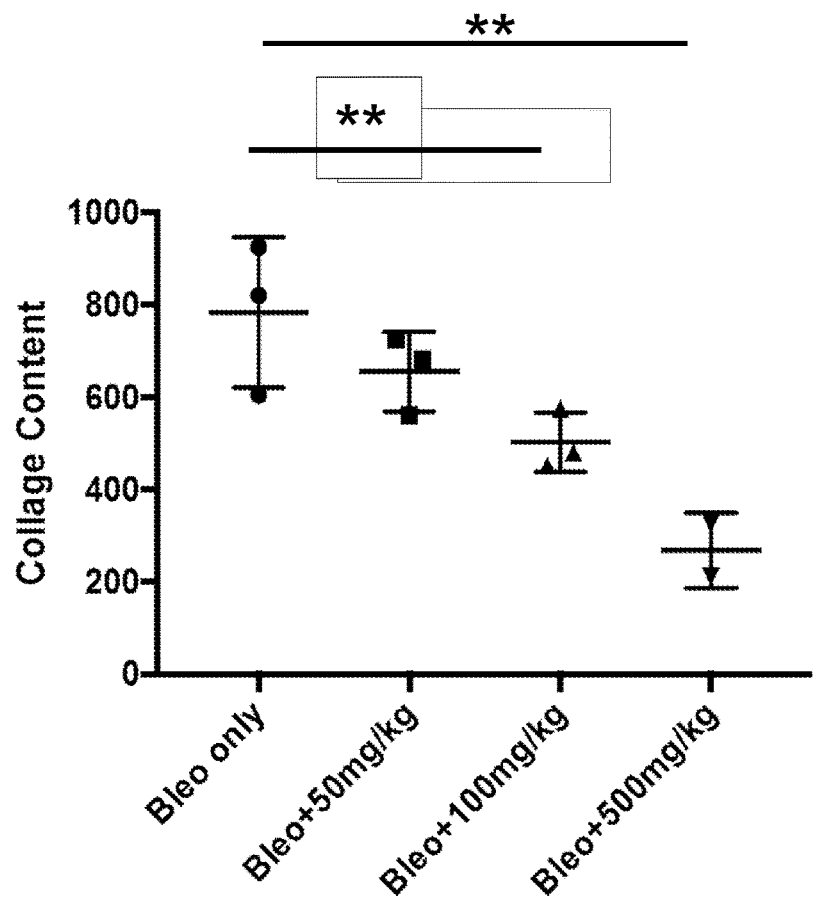

Kasugamycin decreased pulmonary fibrosis (FIG. 2A) and matrix gene expression after bleomycin treatment (FIG. 2B). Kasugamycin also reduced fibrosis in Hermansky Pudlak syndrome (HPS-1 null mice; also called pale ear mice) mice (FIG. 12A-12B) and when given by gavage (FIGS. 13A-13B).

These results demonstrate that kasugamycin, a water soluble antibiotic, is a potent inhibitor of fibrosis in 3 different models of pulmonary fibrosis (IP bleo; IT bleo; transgenic TGFβ1) and in fibrosis prone mice with HPS 1 mutations. Additionally, kasugamcyin is unique amongst aminoglycosides in its ability to inhibit Chit 1.

TGFβ1 is a key mediator of tissue fibrosis and Chit1 regulates fibrosis by regulating the tissue effects of TGFβ1. It is demonstrated herein that the tissue effects of TGFβ1 are mediated by its ability to induce stimulatory Smad 2 and 3 signaling and down regulated by the induction of an inhibitory smad called Smad 7. Additionally, Chit1 induces tissue fibrosis by inhibiting Smad7. Researchers in the field of fibrosis have been looking, for a long time, for a way to regulate fibrosis by regulating Smad 7. It is now demonstrated herein that this can be done by regulating Chit1.

What is claimed herein is:

1. A method of treating pulmonary fibrosis in a subject in need thereof, the method comprising administering kasugamycin or derivatives thereof to the subject, wherein the subject has been determined to have an increased level of Chit1 and/or Chit1 activity.

2. The method of claim 1, wherein the method comprises administering kasugamycin.

3. The method of claim 1, wherein the kasugamycin or derivative thereof is administered orally.

4. The method of claim 1, wherein the pulmonary fibrosis is selected from the group consisting of: idiopathic pulmonary fibrosis; genetic pulmonary fibrosis; chemotherapy-induced pulmonary fibrosis; radiation pulmonary fibrosis; pulmonary fibrosis associated with drug exposure; and interstitial lung disease.

5. The method of claim 4, wherein the interstitial lung disease is associated with exposures selected from the group consisting of: asbestosis, silicosis, and grain exposure.

* * * * *

SEQUENCE LISTING

<160> NUMBER OF SEQ ID NOS: 4

<210> SEQ ID NO 1
<211> LENGTH: 2268
<212> TYPE: DNA
<213> ORGANISM: Homo sapiens

<400> SEQUENCE: 1

```
actcctggct ggggtgggac agggtggcca gataaaagca gagcaggacc tggaaagctg      60
gtttgtatgg gctgcagcct gccgctgagc tgcatcatgg tgcggtctgt ggcctgggca     120
ggtttcatgg tcctgctgat gatcccatgg ggctctgctg caaaactggt ctgctacttc     180
accaactggg cccagtacag acaggggag gctcgcttcc tgcccaagga cttggacccc     240
agcctttgca cccacctcat ctacgccttc gctggcatga ccaaccacca gctgagcacc     300
actgagtgga atgacgagac tctctaccag gagttcaatg gcctgaagaa gatgttcaca     360
gatatggtag ccacggccaa caacgtcag accttttgtca actcggccat caggtttctg     420
cgcaaataca gctttgacgg ccttgacctt gactgggagt acccaggaag ccaggggagc     480
```

-continued

| | |
|---|---|
| cctgccgtag acaaggagcg cttcacaacc ctggtacagg acttggccaa tgccttccag | 540 |
| caggaagccc agacctcagg gaaggaacgc cttcttctga gtgcagcggt tccagctggg | 600 |
| cagacctatg tggatgctgg atacgaggtg acaaaatcg cccagaacct ggattttgtc | 660 |
| aaccttatgg cctacgactt ccatggctct tgggagaagg tcacgggaca taacagcccc | 720 |
| ctctacaaga ggcaagaaga gagtggtgca gcagccagcc tcaacgtgga tgctgctgtg | 780 |
| caacagtggc tgcagaaggg gaccCCtgcc agcaagctga tccttggcat gcctacctac | 840 |
| ggacgctcct tcacactggc ctcctcatca gacaccagag tgggggcccc agccacaggg | 900 |
| tctggcactc caggcccctt caccaaggaa ggagggatgc tggcctacta tgaagtctgc | 960 |
| tcctggaagg gggccaccaa acagagaatc caggatcaga aggtgcccta catcttccgg | 1020 |
| gacaaccagt gggtgggctt tgatgatgtg gagagcttca aaaccaaggt cagctatctg | 1080 |
| aagcagaagg gactgggcgg ggccatggtc tgggcactgg acttagatga ctttgccggc | 1140 |
| ttctcctgca accagggccg ataccccctc atccagacgc tacggcagga actgagtctt | 1200 |
| ccatacttgc cttcaggcac cccagagctt gaagttccaa aaccaggtca gccctctgaa | 1260 |
| cctgagcatg gccccagccc tggacaagac acgttctgcc agggcaaagc tgatgggctc | 1320 |
| tatcccaatc ctcgggaacg gtccagcttc tacagctgtg cagcggggcg gctgttccag | 1380 |
| caaagctgcc cgacaggcct ggtgttcagc aactcctgca atgctgcac ctggaattga | 1440 |
| gtcgctaaag cccctccagt cccagctttg aggctgggcc caggatcact ctacagcctg | 1500 |
| cctcctgggt tttccctggg ggccgcaatc tggctcctgc aggcctttct gtggtcttcc | 1560 |
| tttatccagg ctttctgctc tcagccttgc cttccttttt tctgggtctc ctgggctgcc | 1620 |
| cctttcactt gcaaaataaa tctttggttt gtgcccctct tcccaaagat gtggtgactt | 1680 |
| aagaggctct ctaagcacac tgttgactcc aaaacatccg caggtcagag ccaggtggga | 1740 |
| aggtggtccg tgcaggatgt gccaggccct gtggcaggtc ttgccccatg agtccatatg | 1800 |
| ccagtgggca gtttcagta cacaggtgat ggcagccaga gcgcggcccc aagtgcaaca | 1860 |
| cgttctttgg ttattggctc agaagcctgg aaacaggagc ttctgcggac cttcacgcac | 1920 |
| gtgttattcc caaaatgcca ctagatggca gcagagaaga acttttccct gatttaagcg | 1980 |
| ctctgcgagc agccactcag cattacacta agaattcaga cccctggtac tcaggggtct | 2040 |
| tcgagataaa tcctgtttgg gcccctttgca ggccctatct cacctactgc ccccgttcac | 2100 |
| cagatgaaga aggaacaatg attattctca ctttataggc atttaaactg aagactgatt | 2160 |
| ctaaccaatt ctgagtccag aaccaaggcc tgaaatgggc cagagagcat gcacacggtg | 2220 |
| tcctggttaa ataaagtcat cccaacattc aaaaaaaaaa aaaaaaaa | 2268 |

<210> SEQ ID NO 2
<211> LENGTH: 2325
<212> TYPE: DNA
<213> ORGANISM: Homo sapiens

<400> SEQUENCE: 2

| | |
|---|---|
| actcctggct ggggtgggac agggtggcca gataaaagca gagcaggacc tggaaagctg | 60 |
| gtttgtatgg gctgcagcct gccgctgagc tgcatcatgg tgcggtctgt ggcctgggca | 120 |
| ggtttcatgg tcctgctgat gatcccatgg ggctctgctg caaaactggt ctgctacttc | 180 |
| accaactggg cccagtacag acaggggggag gctcgcttcc tgcccaagga cttggacccc | 240 |
| agcctttgca cccacctcat ctacgccttc gctggcatga ccaaccacca gctgagcacc | 300 |
| actgagtgga atgacgagac tctctaccag gagttcaatg gcctgaagaa gatgaatccc | 360 |

```
aagctgaaga ccctgttagc catcggaggc tggaatttcg gcactcagaa gttcacagat      420
atggtagcca cggccaacaa ccgtcagacc tttgtcaact cggccatcag gtttctgcgc      480
aaatacagct ttgacggcct tgaccttgac tgggagtacc caggaagcca ggggagccct      540
gccgtagaca aggagcgctt cacaaccctg gtacaggact tggccaatgc cttccagcag      600
gaagcccaga cctcagggaa ggaacgcctt cttctgagtg cagcggttcc agctgggcag      660
acctatgtgg atgctggata cgaggtggac aaaatcgccc agaacctgga ttttgtcaac      720
cttatggcct acgacttcca tggctcttgg gagaaggtca cgggacataa cagccccctc      780
tacaagaggc aagaagagag tggtgcagca gccagcctca cgtggatgc tgctgtgcaa       840
cagtggctgc agaaggggac ccctgccagc aagctgatcc ttggcatgcc tacctacgga      900
cgctccttca cactggcctc ctcatcagac accagagtgg gggccccagc acagggtct       960
ggcactccag gcccttcac caaggaagga gggatgctgg cctactatga gtctgctcc       1020
tggaaggggg ccaccaaaca gagaatccag gatcagaagg tgccctacat cttccgggac     1080
aaccagtggg tgggctttga tgatgtggag agcttcaaaa ccaaggtcag ctatctgaag     1140
cagaagggac tgggcgggc catggtctgg gcactggact tagatgactt tgccggcttc      1200
tcctgcaacc agggccgata ccccctcatc cagacgctac ggcaggaact gagtcttcca     1260
tacttgcctt caggcacccc agagcttgaa gttccaaaac caggtcagcc ctctgaacct     1320
gagcatggcc ccagccctgg acaagacacg ttctgccagg gcaaagctga tgggctctat     1380
cccaatcctc gggaacggtc cagcttctac agctgtgcag cggggcggct gttccagcaa     1440
agctgcccga caggcctggt gttcagcaac tcctgcaaat gctgcacctg gaattgagtc     1500
gctaaagccc ctccagtccc agctttgagg ctgggcccag gatcactcta cagcctgcct     1560
cctgggtttt cctgggggc cgcaatctgg ctcctgcagg cctttctgtg gtcttccttt      1620
atccaggctt tctgctctca gccttgcctt ccttttttct gggtctcctg ggctgccct       1680
ttcacttgca aaataaatct ttggtttgtg ccctcttcc caaagatgtg gtgacttaag      1740
aggctctcta gcacactgt tgactccaaa acatccgcag gtcagagcca ggtgggaagg      1800
tggtccgtgc aggatgtgcc aggccctgtg gcaggtcttg ccccatgagt ccatatgcca     1860
gtgggcagtt ccagtacac aggtgatggc agccagagcg cggccccaag tgcaacacgt      1920
tctttggtta ttggctcaga agcctggaaa caggagcttc tgcggacctt cacgcacgtg     1980
ttattcccaa aatgccacta gatggcagca gagaagaact tttccctgat ttaagcgctc     2040
tgcgagcagc cactcagcat tacactaaga attcagaccc ctggtactca ggggtcttcg     2100
agataaatcc tgtttgggcc ctttgcaggc cctatctcac ctactgcccc cgttcaccag     2160
atgaagaagg aacaatgatt attctcactt tataggcatt taaactgaag actgattcta     2220
accaattctg agtccagaac caaggcctga atgggccag agagcatgca cacggtgtcc      2280
tggttaaata aagtcatccc aacattcaaa aaaaaaaaaa aaaaa                     2325
```

<210> SEQ ID NO 3
<211> LENGTH: 447
<212> TYPE: PRT
<213> ORGANISM: Homo sapiens

<400> SEQUENCE: 3

Met Val Arg Ser Val Ala Trp Ala Gly Phe Met Val Leu Leu Met Ile
1               5                   10                  15

Pro Trp Gly Ser Ala Ala Lys Leu Val Cys Tyr Phe Thr Asn Trp Ala

```
            20                  25                  30
Gln Tyr Arg Gln Gly Glu Ala Arg Phe Leu Pro Lys Asp Leu Asp Pro
         35                  40                  45
Ser Leu Cys Thr His Leu Ile Tyr Ala Phe Ala Gly Met Thr Asn His
 50                  55                  60
Gln Leu Ser Thr Thr Glu Trp Asn Asp Glu Thr Leu Tyr Gln Glu Phe
 65                  70                  75                  80
Asn Gly Leu Lys Lys Met Phe Thr Asp Met Val Ala Thr Ala Asn Asn
                 85                  90                  95
Arg Gln Thr Phe Val Asn Ser Ala Ile Arg Phe Leu Arg Lys Tyr Ser
             100                 105                 110
Phe Asp Gly Leu Asp Leu Asp Trp Glu Tyr Pro Gly Ser Gln Gly Ser
             115                 120                 125
Pro Ala Val Asp Lys Glu Arg Phe Thr Thr Leu Val Gln Asp Leu Ala
             130                 135                 140
Asn Ala Phe Gln Gln Glu Ala Gln Thr Ser Gly Lys Glu Arg Leu Leu
145                 150                 155                 160
Leu Ser Ala Ala Val Pro Ala Gly Gln Thr Tyr Val Asp Ala Gly Tyr
                 165                 170                 175
Glu Val Asp Lys Ile Ala Gln Asn Leu Asp Phe Val Asn Leu Met Ala
             180                 185                 190
Tyr Asp Phe His Gly Ser Trp Glu Lys Val Thr Gly His Asn Ser Pro
             195                 200                 205
Leu Tyr Lys Arg Gln Glu Glu Ser Gly Ala Ala Ala Ser Leu Asn Val
             210                 215                 220
Asp Ala Ala Val Gln Gln Trp Leu Gln Lys Gly Thr Pro Ala Ser Lys
225                 230                 235                 240
Leu Ile Leu Gly Met Pro Thr Tyr Gly Arg Ser Phe Thr Leu Ala Ser
                 245                 250                 255
Ser Ser Asp Thr Arg Val Gly Ala Pro Ala Thr Gly Ser Gly Thr Pro
             260                 265                 270
Gly Pro Phe Thr Lys Glu Gly Gly Met Leu Ala Tyr Tyr Glu Val Cys
             275                 280                 285
Ser Trp Lys Gly Ala Thr Lys Gln Arg Ile Gln Asp Gln Lys Val Pro
             290                 295                 300
Tyr Ile Phe Arg Asp Asn Gln Trp Val Gly Phe Asp Asp Val Glu Ser
305                 310                 315                 320
Phe Lys Thr Lys Val Ser Tyr Leu Lys Gln Lys Gly Leu Gly Gly Ala
                 325                 330                 335
Met Val Trp Ala Leu Asp Leu Asp Asp Phe Ala Gly Phe Ser Cys Asn
                 340                 345                 350
Gln Gly Arg Tyr Pro Leu Ile Gln Thr Leu Arg Gln Glu Leu Ser Leu
             355                 360                 365
Pro Tyr Leu Pro Ser Gly Thr Pro Glu Leu Glu Val Pro Lys Pro Gly
             370                 375                 380
Gln Pro Ser Glu Pro Glu His Gly Pro Ser Pro Gly Gln Asp Thr Phe
385                 390                 395                 400
Cys Gln Gly Lys Ala Asp Gly Leu Tyr Pro Asn Pro Arg Glu Arg Ser
                 405                 410                 415
Ser Phe Tyr Ser Cys Ala Ala Gly Arg Leu Phe Gln Gln Ser Cys Pro
             420                 425                 430
Thr Gly Leu Val Phe Ser Asn Ser Cys Lys Cys Cys Thr Trp Asn
             435                 440                 445
```

<210> SEQ ID NO 4
<211> LENGTH: 466
<212> TYPE: PRT
<213> ORGANISM: Homo sapiens

<400> SEQUENCE: 4

```
Met Val Arg Ser Val Ala Trp Ala Gly Phe Met Val Leu Leu Met Ile
1               5                   10                  15

Pro Trp Gly Ser Ala Ala Lys Leu Val Cys Tyr Phe Thr Asn Trp Ala
            20                  25                  30

Gln Tyr Arg Gln Gly Glu Ala Arg Phe Leu Pro Lys Asp Leu Asp Pro
        35                  40                  45

Ser Leu Cys Thr His Leu Ile Tyr Ala Phe Ala Gly Met Thr Asn His
    50                  55                  60

Gln Leu Ser Thr Thr Glu Trp Asn Asp Glu Thr Leu Tyr Gln Glu Phe
65                  70                  75                  80

Asn Gly Leu Lys Lys Met Asn Pro Lys Leu Lys Thr Leu Leu Ala Ile
                85                  90                  95

Gly Gly Trp Asn Phe Gly Thr Gln Lys Phe Thr Asp Met Val Ala Thr
            100                 105                 110

Ala Asn Asn Arg Gln Thr Phe Val Asn Ser Ala Ile Arg Phe Leu Arg
        115                 120                 125

Lys Tyr Ser Phe Asp Gly Leu Asp Leu Asp Trp Glu Tyr Pro Gly Ser
    130                 135                 140

Gln Gly Ser Pro Ala Val Asp Lys Glu Arg Phe Thr Thr Leu Val Gln
145                 150                 155                 160

Asp Leu Ala Asn Ala Phe Gln Gln Glu Ala Gln Thr Ser Gly Lys Glu
                165                 170                 175

Arg Leu Leu Leu Ser Ala Ala Val Pro Ala Gly Gln Thr Tyr Val Asp
            180                 185                 190

Ala Gly Tyr Glu Val Asp Lys Ile Ala Gln Asn Leu Asp Phe Val Asn
        195                 200                 205

Leu Met Ala Tyr Asp Phe His Gly Ser Trp Glu Lys Val Thr Gly His
    210                 215                 220

Asn Ser Pro Leu Tyr Lys Arg Gln Glu Glu Ser Gly Ala Ala Ala Ser
225                 230                 235                 240

Leu Asn Val Asp Ala Ala Val Gln Gln Trp Leu Gln Lys Gly Thr Pro
                245                 250                 255

Ala Ser Lys Leu Ile Leu Gly Met Pro Thr Tyr Gly Arg Ser Phe Thr
            260                 265                 270

Leu Ala Ser Ser Ser Asp Thr Arg Val Gly Ala Pro Ala Thr Gly Ser
        275                 280                 285

Gly Thr Pro Gly Pro Phe Thr Lys Glu Gly Gly Met Leu Ala Tyr Tyr
    290                 295                 300

Glu Val Cys Ser Trp Lys Gly Ala Thr Lys Gln Arg Ile Gln Asp Gln
305                 310                 315                 320

Lys Val Pro Tyr Ile Phe Arg Asp Asn Gln Trp Val Gly Phe Asp Asp
                325                 330                 335

Val Glu Ser Phe Lys Thr Lys Val Ser Tyr Leu Lys Gln Lys Gly Leu
            340                 345                 350

Gly Gly Ala Met Val Trp Ala Leu Asp Leu Asp Asp Phe Ala Gly Phe
        355                 360                 365

Ser Cys Asn Gln Gly Arg Tyr Pro Leu Ile Gln Thr Leu Arg Gln Glu
```

-continued

```
            370                 375                 380
Leu Ser Leu Pro Tyr Leu Pro Ser Gly Thr Pro Glu Leu Glu Val Pro
385                 390                 395                 400

Lys Pro Gly Gln Pro Ser Glu Pro Glu His Gly Pro Ser Pro Gly Gln
                405                 410                 415

Asp Thr Phe Cys Gln Gly Lys Ala Asp Gly Leu Tyr Pro Asn Pro Arg
                420                 425                 430

Glu Arg Ser Ser Phe Tyr Ser Cys Ala Ala Gly Arg Leu Phe Gln Gln
                435                 440                 445

Ser Cys Pro Thr Gly Leu Val Phe Ser Asn Ser Cys Lys Cys Cys Thr
    450                 455                 460

Trp Asn
465
```